United States Patent
Ni et al.

(10) Patent No.: US 6,586,210 B1
(45) Date of Patent: *Jul. 1, 2003

(54) POLYNUCLEOTIDES ENCODING T1 RECEPTOR LIKE LIGAND II

(75) Inventors: Jian Ni, Rockville, MD (US); Reiner L. Gentz, Silver Spring, MD (US); Steven M. Ruben, Olney, MD (US)

(73) Assignee: Human Genome Sciences, Inc., Rockville, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/916,442

(22) Filed: Aug. 22, 1997

Related U.S. Application Data

(60) Provisional application No. 60/024,348, filed on Aug. 23, 1996.

(51) Int. Cl.[7] .......................... C12N 5/10; C12N 15/19; C12N 15/63
(52) U.S. Cl. .................... 435/69.5; 435/71.1; 435/71.2; 435/471; 435/252.3; 435/325; 435/320.1; 435/252.33; 435/252.8; 435/358; 435/365; 536/23.5; 536/24.3; 536/24.31
(58) Field of Search ................................ 536/235, 24.3, 536/24.31; 435/69.1, 69.5, 69.51, 252.3, 320.1, 71.1, 71.2, 471, 325, 252.33, 252.8, 358, 365

(56) References Cited

U.S. PATENT DOCUMENTS 5,576,191 A * 11/1996 Gayle et al. ................ 435/691
5,767,065 A     6/1998 Mosley et al.

FOREIGN PATENT DOCUMENTS

WO    WO 94/17187    8/1994

OTHER PUBLICATIONS

Bergers, G. et al., "Alternative promoter usage of the Fos–responsive gene *Fit–1* generates mRNA isoforms coding for either secreted or membrane–bound proteins related to the IL–1 receptor," *EMBO J.* 13(5):1176–1188 (1994).

Bird, T.A. et al., "Evidence that MAP (Mitogen–Activated Protein) Kinase Activation may be a Necessary but Not Sufficient Signal for a Restricted Subset of Responses in IL–1–Treated Epidermoid Cells," *Cytokine* 4(6):429–440 (1992).

Cleary, M.L. et al., "Cloning and Structural Analysis of cDNAs for bcl–2 and a Hybrid bcl–2/Immunoglobulin Transcript Resulting from the t(14;18) Translocation," *Cell* 47:19–28 (1986).

Eldon, E. et al., "The *Drosophila 18 wheeler* is required for morphogenesis and has striking similarities to *Toll,*" *Development* 120 (4):885–899 (1994).

Fleischmann, R.D. et al., "Whole–Genome Random Sequencing and Assembly of *Haemophilus influenzae* Rd," *Science* 269:496–512 (Jul. 1995).

Gay, N.J. and F.J. Keith, "*Drosophila* Toll and IL–1 receptor," *Nature* 351:355–356 (1991).

Gayle, M.A. et al., "Cloning of a Putative Ligand for the T1/ST2 Receptor," *J. Biol. Chem.* 271(10):5784–5789 (Mar. 1996).

Greenfeder, S.A. et al., "Molecular Cloning and Characterization of a Second Subunit of the Interleukin 1 Receptor Complex," *J. Biol. Chem.* 270(23):13757–13765 (Jun. 1995).

Hashimoto, C. et al., "The *Toll* Gene of *Drosophila*, Required for Dorsal–Ventral Embryonic Polarity, Appears to Encode a Transmembrane Protein," *Cell* 52:269–279 (1988).

Hopp, T.P., "Evidence from sequence information that the interleukin–1 receptor is a transmembrane GTPase," *Protein Science* 4(9): 1851–1859 (Sep. 1995).

Klemenz, R. et al., "Serum– and oncoprotein–mediated induction of a gene with sequence similarity to the gene encoding carcinoembryonic antigen," *Proc. Natl. Acad. Sci. USA* 86(15):5708–5712 (1989).

Kumar, S. et al., "ST2/T1 Protein Functionally Binds to Two Secreted Proteins from Balb/c 3T3 and Human Umbilical Vein Endothelial Cells but Does Not Bind Interleukin 1," *J. Biol. Chem.* 270(46):27905–27913 (Nov. 1995).

Lord, K.A. et al., "Nucleotide sequence and expression of a cDNA encoding MyD88, a novel myeloid differentiation primary response gene induced by IL6," *Oncogene* 5(7):1095–1097 (1990).

Mitcham, J.L. et al., "T1/ST2 Signaling Establishes It as a Member of Expanding Interleukin–1 Receptor Family," *J. Biol. Chem.* 271(10):5777–5783 (Mar. 1996).

Nomura N. et al., "Prediction of the Coding Sequences of Unidentified Human Genes. I. The Coding Sequences of 40 New Genes (KIAA0001–KIAA0040) Deduced by Analysis of Randomly Sampled cDNA Clones from Human Immature Myeloid Cell Line KG–1," *DNA Res.* 1:27–35 (1994).

(List continued on next page.)

*Primary Examiner*—Prema Mertz
(74) *Attorney, Agent, or Firm*—Human Genome Services, Inc.

(57) ABSTRACT

The present invention concerns a novel T1R-like ligand II protein. In particular, isolated nucleic acid molecules are provided encoding the T1R-like ligand II protein. T1R-like ligand II polypeptides are also provided, as are recombinant vectors and host cells for expressing the same.

62 Claims, 4 Drawing Sheets

OTHER PUBLICATIONS

Ostrowski, J. et al., "A Serine/Threonine Kinase Activity Is Closely Associated with a 65–kDa Phosphoprotein Specifically Recognized by the κB Enhancer Element," *J. Biol. Chem.* 266(19):12722–12733 (1991).

Parnet, P. et al., "IL–1Rrp Is a Novel Receptor–like Molecule Similar to the Type I Interleukin–1 Receptor and Its Homologues T1/ST2 and IL–1R AcP," *J. Biol. Chem.* 271(8):3967–3970 (Feb. 1996).

Reikerstorfer, A. et al., "Low Affinity Binding of Interleukin–1β and Intracellular Signaling via NF–κB Identify Fit–1 as a Distant Member of the Interleukin–1 Receptor Family," *J. Biol. Chem.* 270(30):17645–17648 (Jul. 1995).

Schneider, D.S. et al., "Dominant and recessive mutations define functional domains of *Toll*, a transmembrane protein required for dorsal–ventral polarity in the *Drosophila* embryo," *Genes & Dev.* 5:797–807 (1991).

Sims, J.E. et al., "cDNA Expression Cloning of the IL–1 Receptor, a Member of the Immunoglobulin Superfamily," *Science* 241:585–589 (1988).

Sims, J.E. et al., "Genomic Organization of the Type I and Type II IL–1 Receptors," *Cytokine* 7(6):483–490 (Aug. 1995).

Tominaga, S., "A putative protein of a growth specific cDNA from BALB/c–3T3 cells in highly similar to the extracellular portion of mouse interleukin 1 receptor," *FEBS Lett.* 258(2):301–304 (1989).

Yanagisawa, K. et al., "Presence of a novel primary response gene ST2L, encoding a product highly similar to the interleukin 1 receptor type 1," *FEBS Lett.* 318(1):83–87 (1993).

International Search Report for Application No. PCT/US96/13768, mailed Jan., 1997.

Database EST–STS on MASPAR search, WashU–Merck EST Project (St Louis MO, USA) No. H50051, from Hillier et al., "yo26g04.r1 *Homo sapiens* cDNA clone 179094 5'," (Sep. 1995).

Database EST–STS on MASPAR search, WashU–Merck EST Project (St Louis MO, USA) No. T48838, from Hillier et al., "yb05e06.r1 *Homo sapiens* cDNA clone 70306 5'," (Feb. 1995).

Database EST–STS on MAPSAR search, Research Institute, Otsuka Pharmaceutical Co. Ltd. (Kagasuno Kawauchi–cho Tokushima, Japan) No. D81710, from Fujiwara et al., "Human fetal brain cDNA 5' –end GEN–401D07" (Nov. 1995).

Genbank Report, Accession No. AA013099, submitted by Hillier et al. (Nov. 1996).

Genbank Report, Accession No. AA251084, submitted by National Cancer Institute, Cancer Genome Anatomy Project (CGAP) (Aug. 1997).

Genbank Report, Accession No. R58562, submitted by Hwang et al. (May 1996).

Genbank Report, Accession No. N28878, submitted by Hillier et al. (Jan. 1996).

Genbank Report, Accession No. AA019348, submitted by Hillier et al. (Aug. 1996).

Genbank Report, Accession No. N49615, submitted by Hillier et al. (Feb. 1996).

Genbank Report, Accession No. AA112675, submitted by Hillier et al. (Aug. 1997).

Genbank Report, Accession No. AA082161, submitted by Hillier et al. (Jul. 1997).

Genbank Report, Accession No. H03613, submitted by Hillier et al. (Jun. 1995).

Genbank Report, Accession No. R54717, submitted by Hillier et al. (May 1995).

Genbank Report, Accession No. H27167, submitted by Hillier et al. (Jul. 1995).

Genbank Report, Accession No. AA188741, submitted by Hillier et al. (Jan. 1997).

Genbank Report, Accession No. AA094735, submitted by Liew, C.C. (Oct. 1996).

Genbank Report, Accession No. AA285143, submitted by National Cancer Institute, Cancer Genome Anatomy Project (CGAP) (Aug. 1997).

NCBI Entrez, GenBank Report, Accession No. R54718, from Hillier, L. et al. (May 1995).

NCBI Entrez, GenBank Report, Accession No. H03503, from Hillier, L. et al. (Jun. 1995).

NCBI Entrez, GenBank Report, Accession No. H27168, from Hillier, L. et al. (Jul. 1995).

NCBI Entrez, GenBank Report, Accession No. N21637, from Hillier, L. et al. (Dec. 1995).

NCBI Entrez, GenBank Report, Accession No. N34911, from Hillier, L. et al. (Jan. 1996).

NCBI Entrez, GenBank Report, Accession No. N45687, from Hillier, L. et al. (Feb. 1996).

NCBI Entrez, GenBank Report, Accession No. N46921, from Hillier, L. et al. (Feb. 1996).

NCBI Entrez, GenBank Report, Accession No. W58982, from Marra, M. et al. (Jun. 1996).

NCBI Entrez, GenBank Report, Accession No. AA003600, from Marra, M. et al. (Jul. 1996).

NCBI Entrez, GenBank Report, Accession No. C16937, from Fujiwara, T. et al. (Sep. 1996).

NCBI Entrez, GenBank Report, Accession No. AA089688, from Liew, C.C. (Oct. 1996).

NCBI Entrez, GenBank Report, Accession No.AA097327, from Marra, M. et al. (Feb. 1997).

NCBI Entrez, GenBank Report, Accession No. AA097350, from Marra, M. et al. (Feb. 1997).

NCBI Entrez, GenBank Report, Accession No. AA186155, from Marra, M. et al. (Feb. 1997).

NCBI Entrez, GenBank Report, Accession No. AA288199, from Marra, M. et al. (Apr. 1997).

NCBI Entrez, GenBank Report, Accession No. AA381943, from Adams, M.D. et al. (Apr. 1997).

NCBI Entrez, GenBank Report, Accession No. AA413599, from Marra, M. et al. (Aug. 1997).

NCBI Entrez, GenBank Report, Accession No. AA393405, from Hillier, L. et al. (Aug. 1997).

NCBI Entrez, GenBank Report, Accession No. AA397587, from Hillier, L. et al. (Aug. 1997).

NCBI Entrez, GenBank Report, Accession No. AA400773, from Hillier, L. et al. (Aug. 1997).

NCBI Entrez, GenBank Report, Accession No. AA251721, from NCI–CGAP (Aug. 1997).

NCBI Entrez, GenBank Report, Accession No. AA287714, from NCI–CGAP (Aug. 1997).

NCBI Entrez, GenBank Report, Accession No. AA287713, from NCI–CGAP (Aug. 1997).

NCBI Entrez, GenBank Report, Accession No. AA421135, from Hillier, L. et al. (Nov. 1997).

NCBI Entrez, GenBank Report, Accession No. AA668793, from NCI–CGAP (Nov. 1997).
NCBI Entrez, GenBank Report, Accession No. AA694551, from NCI–CGAP (1998).
NCBI Entrez, GenBank Report, Accession No. AA743312, from NCI–CGAP (1998).

Pir56 database, Accession No. S54622, de Haan et al. (Jul. 1995).

Stomes et al, *DNAS* V 92, 1995, p8011–8015.*

* cited by examiner

```
              10                    30                    50
              .                     .                     .
CACGAGGACAACAGTACCTGACGCCTCTTTCAGCCCGGGATCGCCCCAGCAGGGATGGGC
                                                         M  G 70                    90                   110
              .                     .                     .
GACAAGATCTGGCTGCCCTTCCCCGTGCTCCTTCTGGCCGCTCTGCCTCCGGTGCTGCTG
 D  K  I  W  L  P  F  P  V  L  L  L  A  A  L  P  P  V  L  L 130                   150                   170
              .                     .                     .
CCTGGGGCGGCCGGCTTCACACCTTCCCTCGATAGCGACTTCACCTTTACCCTTCCCGCC
 P  G  A  A  G  F  T  P  S  L  D  S  D  F  T  F  T  L  P  A 190                   210                   230
              .                     .                     .
GGCCAGAAGGAGTGCTTCTACCAGCCCATGCCCCTGAAGGCCTCGCTGGAGATCGAGTAC
 G  Q  K  E  C  F  Y  Q  P  M  P  L  K  A  S  L  E  I  E  Y 250                   270                   290
              .                     .                     .
CAAGTTTTAGATGGAGCAGGATTAGATATTGATTTCCATCTTGCCTCTCCAGAAGGCAAA
 Q  V  L  D  G  A  G  L  D  I  D  F  H  L  A  S  P  E  G  K 310                   330                   350
              .                     .                     .
ACCTTAGTTTTTGAACAAAGAAAATCAGATGGAGTTCACACTGTAGAGACTGAAGTTGGT
 T  L  V  F  E  Q  R  K  S  D  G  V  H  T  V  E  T  E  V  G 370                   390                   410
              .                     .                     .
GATTACATGTTCTGCTTTGACAATACATTCAGCACCATTTCTGAGAAGGTGATTTTCTTT
 D  Y  M  F  C  F  D  N  T  F  S  T  I  S  E  K  V  I  F  F 430                   450                   470
              .                     .                     .
GAATTAATCCTGGATAATATGGGAGAACAGGCACAAGAACAAGAAGATTGGAAGAAATAT
 E  L  I  L  D  N  M  G  E  Q  A  Q  E  Q  E  D  W  K  K  Y 490                   510                   530
              .                     .                     .
ATTACTGGCACAGATATATTGGATATGAAACTGGAAGACATCCTGGAATCCATCAACAGC
 I  T  G  T  D  I  L  D  M  K  L  E  D  I  L  E  S  I  N  S 550                   570                   590
              .                     .                     .
ATCAAGTCCAGACTAAGCAAAAGTGGGCACATACAAACTCTGCTTAGAGCATTTGAAGCT
 I  K  S  R  L  S  K  S  G  H  I  Q  T  L  L  R  A  F  E  A
```

FIG.1A

```
         610                   630                   650
          .                     .                     .
CGTGATCGAAACATACAAGAAAGCAACTTTGATAGAGTCAATTTCTGGTCTATGGTTAAT
 R  D  R  N  I  Q  E  S  N  F  D  R  V  N  F  W  S  M  V  N 670                   690                   710
          .                     .                     .
TTAGTGGTCATGGTGGTGGTGTCAGCCATTCAAGTTTATATGCTGAAGAGTCTGTTTGAA
 L  V  V  M  V  V  V  S  A  I  Q  V  Y  M  L  K  S  L  F  E 730                   750                   770
          .                     .                     .
GATAAGAGGAAAAGTAGAACTTAAAACTCCAAACTAGAGTACGTAACATTGAAAAATGAG
 D  K  R  K  S  R  T  *

790                   810                   830
          .                     .                     .
GCATAAAAATGCCATAAACTGTTACAGTCCAGACCATTAATGGTCTTCTCCAAAATATTT 850                   870                   890
          .                     .                     .
TGAGATATAAAAGTAGGAAACAGGTATAATTTTAATGTGAAAATTAAGTCTTCACTTTCT 910                   930                   950
          .                     .                     .
GTGCAAGTAATCCTGCTGATCCAGTTGTACTTAAGTGTGTAACAGGAATATTTTGCAGAA 970                   990                   1010
          .                     .                     .
TATAGGTTTAACTGAATGAAGCCATATTAATAACTGCATTTTCCTAACTTTGAAAAATTT 1030                  1050                  1070
          .                     .                     .
TGCAAATGTCTTAGGTGATTTAAATAAATGAGTATTGGGCCTAATTGCAACACCAGTCTG 1090                  1110                  1130
          .                     .                     .
TTTTTAACAGGTTCTATTACCCAGAACTTTTTTGTAAATGCGGCAGTTACAAATTAACTG 1150                  1170                  1190
          .                     .                     .
TGGAAGTTTTCAGTTTTAAGTTATAAATCACCTGAGAATTACCTAATGATGGATTGAATA 1210                  1230
          .                     .
AATCTTTAGACTACAAAAAAAAAAAAAAAAAAAAAAAAAAAAA
```

FIG.1B

```
1    .MGDKIWLPFPVLLLAALPPVLLPGAAGFTPSLDSDFTFTLPAGQKECFY    49
     |:.    |:::::||  :||| : :|| .|   |::||| ||||.|:|||
1    MMAAGAALALALWLL..MPPVEV.GGAGPPPIQDGEFTFLLPAGRKQCFY    47

50   QPMPLKASLEIEYQVLDGAGLDIDFHLASPEGKTLVFEQRKSDGVHTVE.    98
     |. | .||||.||||::|||||:|| |.||:|  || |  ||.|||||||
48   QSAPANASLETEYQVIGGAGLDVDFTLESPQGVLLVSESRKADGVHTVEP   97

99   TEVGDYMFCFDNTFSTISEKVIFFELILDNMGEQAQEQEDWKKYITGTDI   148
     ||.|||.:||||.|||||||::|||||:|.:.:: :| |:| . :....::
98   TEAGDYKLCFDNSFSTISEKLVFFELIFDSLQDD.EEVEGWAEAVEPEEM   146

149  LDMKLEDILESINSIKSRLSKSGHIQTLLRAFEARDRNIQESNFDRVNFW   198
     ||:|:||| |||:..::.||.:|:::::|||||||||||:||:|::||||
147  LDVKMEDIKESIETMRTRLERSIQMLTLLRAFEARDRNLQEGNLERVNFW   196

199  SMVNLVVMVVVSAIQVYMLKSLFEDKRKSRT.   229
     |  ||:.|:::|..:||: ||.:|:|||. .||
197  SAVNVAVLLLVAVLQVCTLKRFFQDKRPVPT.   227
```

POLYNUCLEOTIDES ENCODING T1 RECEPTOR LIKE LIGAND II

CROSS-REFERENCE TO RELATED APPLICATION

This application claims priority benefit to U.S. application Ser. No. 60/024,348, filed Aug. 23, 1996, which disclosure is herein incorporated by reference.

BACKGROUND OF THE INVENTION

1. Field of the Invention

The present invention concerns a novel T1 Receptor (T1R)-like ligand II protein. In particular, isolated nucleic acid molecules are provided encoding the T1R-like ligand II protein. T1R-like ligand II polypeptides are also provided, as are recombinant vectors and host cells for expressing the same.

2. Related Art

Interleukin-1 (IL-1). Interleukin-1 (IL-1α and IL-1β) is a "multifunctional" cytokine that affects nearly every cell type, and often in concert with other cytokines or small mediator molecules. (Dinarello, C. A., *Blood* 87:2095–2147 (Mar. 15, 1996).) There are three members of the IL-1 gene family: IL-1α, IL-1β, and IL-1 receptor antagonist (IL-1Ra). IL-1α and IL-1β are agonists and IL-1Ra is a specific receptor antagonist. IL-1α and β are synthesized as precursors without leader sequences. The molecular weight of each precursor is 31 kD. Processing of IL-1α or IL-1β to "mature" forms of 17 kD requires specific cellular proteases. In contrast, IL-1Ra evolved with a signal peptide and is readily transported out of the cells and termed secreted IL-1Ra (sIL-1Ra).

IL-1 Receptor and Ligands. The receptors and ligands of the IL-1 pathway have been well defined (for review, see Dinarello, C. A., *FASEB J.* 8:1314–1325 (1994); Sims, J. E. et al., *Interleukin-1 signal transduction: Advances in Cell and Molecular Biology of Membranes and Organelles,* Vol. 3, JAI Press, Inc., Greenwich, Conn. (1994), pp. 197–222). Three ligands, IL-1α, IL-1β, and IL1 receptor antagonist (IL-1Ra) bind three forms of IL1 receptor, an 80-kDa type I IL-1 receptor (IL-RI) (Sims, J. E. et al., *Science* 241:585–589 (1988)), a 68-kDa type II IL-1 receptor (IL-1RII) (McMahan, C. J. et al., *EMBO J.* 10:2821–2832 (1991)), and a soluble form of the type II IL-1R (sIL-1RII) (Colotta, F. et al., *Science* 261:472–475 (1993)).

The interactions between the IL-1 ligands and receptors play an essential role in the stimulation and regulation of the IL-1-mediated host response to injury and infection. Cells expressing IL-1RI and treated with IL-1α or IL-1β respond in several specific ways, including stimulating nuclear localization of the rel-related transcription factor, NF-κβ(for review, see Thanos, D. & Maniatis, T., *Cell* 80:529–532 (1996)), activation of protein kinases of the mitogen-activated protein kinase superfamily that phosphorylate residue threonine 669 (Thr-669) of the epidermal growth factor receptor (EGFR) (Guy, G. R. et al., *J. Biol. Chem.* 267:184–1852 (1992); Bird, T. A. et al., *J. Biol. Chem.* 268:222861–22870 (1991); Bird, T. A. et al., *J. Biol. chem.* 269:31836–31844 (1994)), and stimulation of transcription of the EL-8 gene (Mukaida, N. et al., *J. Biol. Chem.* 265:21128–21133 (1990)).

IL-1RI-like family. Many proteins from diverse systems show homology to the cytoplasmic domain of the IL-1RI. This expanding IL-1RI-like family includes mammalian proteins, Drosophila proteins, and a plant (tobacco) protein. (Gay, N.J. & Keith, F. J., *Nature* 351:355–356 (1991); Hashimoto, C. et al., *Cell* 52:269–279 (1988); Schneider, D. S. et al., *Genes & Dev.* 5:797–807 (1991); Edon, E. et al., *Development* 120:885–899 (1994); Mitchan, J. L. et al., *J. Biol. Chem* 271:5777–5782 (Mar. 8, 1996)).

The mammalian IL-1RI-like receptor family members include a murine protein MyD88 (Lord, K. A. et al., *Oncogene* 5:1095–1097 (1990)) and a human gene, rsc786 (Nomura, N. et al., *DNA Res.* 1:27–35 (1994)). Another murine receptor member, T1/ST2, was previously characterized as a novel primary response gene expressed in BALB/c-3T3 cells (Klemenz, R. et al., *Proc. Natl. Acad. Sci. USA* 86:5708–5712 (1989); Tominaga, S., *FEBS Lett.* 258:301–304 (1989); Tominaga, S. et al., *FEBS Lett.* 318:83–87(1993)). The transmembrane protein muIL-1R AcP (Greenfeder, S. A. et al., *J. Biol Chem.* 270:13757–13765 (1995)) has homology to both the type I and type II IL-1R. IL-1R AcP has recently been shown to increase the affinity of IL-1RI for IL-1β and may be involved in mediating the IL-1 response.

T1 Receptors. T1/ST2 receptors (hereinafter, "T1 receptors"), as a member of the IL-1 receptor family (Bergers, G., et al., *EMBO J.* 13:1176 (1994)), have various homologs in different species. In the rat, it is called Fit-1, an estrogen-inducible, c-fos-dependent transmembrane protein that shares 26% to 29% amino acid homology to the mouse IL-1RI and II, respectively. In the mouse, the Fit-1 protein is called ST2 and in the human it is called T1. The organization of the two IL-1 receptors and the Fit-1/ST2/T1 genes indicates they are derived from a common ancestor (Sims, J. E., et al., *Cytokine* 7:483 (1995)). Fit-1 exists in two forms: a membrane form (Fit-1M) with a cytosolic domain similarly to that of the IL-1RI and Fit-1S, which is secreted and composed of the extracellular domain of Fit-M.

In many ways, these two forms of the Fit-1 protein are similar to those of the membrane-bound and soluble IL-1RI. It has been shown that the IL-1sRI is derived from proteolytic cleavage of the cell-bound form (Sims, J. E., et al., *Cytokine* 7:483 (1995)). On the other hand, the Fit-1 gene is under the control of two promoters, which results in two isoforms coding for either the membrane or soluble form of the receptor. Two RNA transcripts result from alternative RNA splicing of the 3' end of the gene. Although IL-1β binds weakly to Fit-1 and does not transduce a signal (Reikerstorger, A., et al., *J. Biol. Chem.* 270:17645 (1995)), a chimeric receptor consisting of the extracellular murine IL-1RI fused to the cytosolic Fit-1 transduces an IL-1 signal (Reikerstorger, A., et al., *J. Biol. Chem.* 270:17645 (1995)). The cytosolic portion of Fit-1 align with GTPase-like sequences of IL-1RI (Hopp, T. P., *Protein Sci.* 4:1851 (1995)) (see below).

IL1 production in various disease states. Increased IL-1 production has been reported in patients with various viral, bacterial, fungal, and parasitic infections; intravascular coagulation; high-dose IL-2 therapy; solid tumors; leukemias; Alzheimer's disease; HIV-1 infection; autoimmune disorders; trauma (surgery); hemodialysis; ischemic diseases (myocardial infarction); noninfectious hepatitis; asthma; UV radiation; closed head injury; pancreatitis; periodontitis; graft-versus-host disease; transplant rejection; and in healthy subjects after strenuous exercise. There is an association of increased IL-1β production in patients with Alzheimer's disease and a possible role for IL-1 in the release of the amyloid precursor protein (Vasilakos, J. P., et al., *FEBS Lett.* 354:289 (1994)). However, in most conditions, IL-1 is not the only cytokine exhibiting increased production and hence the specificity of the IL-1 findings as related to the pathogenesis of any particular disease is lacking. In various disease states, IL-1β, but not IL-1α, is detected in the circulation.

IL-1 in Therapy. Although IL-1 has been found to exhibit many important biological activities, it is also found to be toxic at doses that are close to therapeutic dosages (Dinarello, C. A., Blood 87:2095–2147 (Mar. 15, 1996)). In general, the acute toxicities of either isoform of IL-1 were greater after intravenous compared with subcutaneous injection. Subcutaneous injection was associated with significant local pain, erythema, and swelling (Kitamura, T., & Takaku, F., Exp. Med 7:170 (1989); Laughlin, M. J., Ann. Hematol. 67:267 (1993)). Patients receiving intravenous IL-1 at doses of 100 ng/kg or greater experienced significant hypotension. In patients receiving IL-1β from 4 to 32 ng/kg subcutaneously, there was only one episode of hypotension at the highest dose level (Laughlin, M. J., Ann. Hematol. 67:267 (1993)).

Contrary to IL-1-associated myelostimulation in patients with normal marrow reserves, patients with aplastic anemia treated with 5 daily doses of IL-1α (30 to 100 ng/kg) had no increases in peripheral blood counts or bone marrow cellularity (Walsh, C. E., et al., Br. J. Haematol 80:106 (1992)). IL-1 has been administered to patients undergoing various regiments of chemotherapy to reduce the nadir of neutropenia and thrombocytopenia.

Daily treatment with 40 ng/kg IL-1α from day 0 to day 13 of autologous bone marrow or stem cells resulted in an earlier recovery of neutropenia (median, 12 days; P<0.001) (Weisdorf, D., et al., Blood 84:2044 (1994)). After 14 days of treatment, the bone marrow was significantly enriched with committed myeloid progenitor cells. Similar results were reported in patients with AML receiving 50 ng/kg/d of IL-1β for 5 days starting at the time of transplantation with purged or nonpurged bone marrow (Nemunaitis, J., et al., Blood 83:3473 (1994)). Injecting humans with low doses of either EL-1α or IL-1β confirms the impressive pyrogenic and hypotension-inducing properties of the molecules.

Amelioration of Disease Using Soluble IL-1 Receptors. Administration of murine IL-1sRI to mice has increased the survival of heterotopic heart allografts and reduced the hyperplastic lymph node response to allogeneic cells (Fanslow, W. C., et al., Science 248:739 (1990)). In a rat model of antigen-induced arthritis, local instillation of the murine IL-1sRI reduced joint swelling and tissue destruction (Dower, S. K., et al., Therapeutic Immunol. 1:113 (1994)). These data suggest that the amount of IL-1sRI administered in the normal, contralateral joint was acting systemically. In a model of experimental autoimmune encephalitits, the IL-1sRI reduced the severity of this disease (Jacobs, C. A., et al., J. Immunol. 146:2983 (1991)).

SUMMARY OF THE INVENTION

The present invention provides isolated nucleic acid molecules comprising a polynucleotide encoding a human T1 receptor-(T1R-)like ligand II polypeptide having the amino acid sequence in FIGS. 1A–B (SEQ ID NO:2). The T1R-like ligand II contains an open reading frame encoding a polypeptide of about 229 amino acid residues including an N-terminal methionine, a leader sequence of about 26 amino acid residues, an extracellular mature domain of about 168 residues, a transmembrane domain of about 23 residues and an intracellular domain of about 12 amino acid residues, and a deduced molecular weight of about 26 kDa. The 203 amino acid sequence of the expected mature T1R-like ligand II protein is shown in SEQ ID NO:2 (amino acid residues 1–203).

The invention also provides isolated nucleic acid molecules encoding an T1R-like ligand II having an amino acid sequence encoded by the cDNA of the clone deposited as ATCC Deposit No. 97655 on Jul. 12, 19961. Preferably, the nucleic acid molecule will encode the mature polypeptide encoded by the above-described deposited cDNA.

Thus, one aspect of the invention provides an isolated nucleic acid molecule comprising a polynucleotide having a nucleotide sequence selected from the group consisting of: (a) a nucleotide sequence encoding the T1R-like ligand II polypeptide having the complete amino acid sequence in SEQ ID NO:2; (b) a nucleotide sequence encoding the T1R-like ligand II polypeptide having the complete amino acid sequence in SEQ ID NO:2 but minus the N-terminal methionine residue nucleotide sequence encoding the mature T1R-1 like ligand II poly peptide having the amino acid sequence at positions from about 1 to about 203 in SEQ ID NO:2; (d) a nucleotide sequence encoding the T1R-like ligand II polypeptide having the complete amino acid sequence encoded by the cDNA clone contained in ATCC Deposit No. 97655; (e) a nucleotide sequence encoding the mature T1R-like ligand II polypeptide having the amino acid sequence encoded by the cDNA clone contained in ATCC Deposit No. 97655; and (f) a nucleotide sequence complementary to any of the nucleotide sequences in (a), (b), (c), (d), or (e) above.

Further embodiments of the invention include isolated nucleic acid molecules that comprise a polynucleotide having a nucleotide sequence at least 95% identical, and more preferably at least 96%, 97%, 98% or 99% identical, to any of the nucleotide sequences in (a), (b), (c), (d), (e), or (f), above, or a polynucleotide which hybridizes under stringent hybridization conditions to a polynucleotide in (a), (b), (c), (d), (e), or (f), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a T1R-like ligand II polypeptide having an amino acid sequence in (a), (b), (c), (d), or (e), above.

The present invention also relates to recombinant vectors which include the isolated nucleic acid molecules of the present invention, host cells containing the recombinant vectors, and the production of T1R-like ligand II polypeptides or fragments thereof by recombinant techniques.

The invention further provides an isolated T1R-like ligand II polypeptide having an amino acid sequence selected from the group consisting of: (a) the amino acid sequence of the T1R-like ligand II polypeptide having the complete 229 amino acid sequence, including the leader sequence shown in SEQ ID NO:2; (b) the amino acid sequence of the T1R-like ligand II polypeptide having the complete 229 amino acid sequence, including the leader sequence shown in SEQ ID NO:2 but minus the N-terminal methionine residue; (c) the amino acid sequence of the mature T1R-like ligand H polypeptide (without the leader) having the amino acid sequence at positions 1 to 203 in SEQ ID NO:2; (d) the amino acid sequence of the T1R-like ligand II polypeptide having the complete amino acid sequence, including the leader, encoded by the cDNA clone contained in ATCC Deposit No. 97655; and (e) the amino acid sequence of the mature T1R-1 like ligand II polypeptide having the amino acid sequence encoded by the cDNA clone contained in ATCC Deposit No. 97655. The polypeptides of the present invention also include polypeptides having an amino acid sequence at least 95% identical, and more preferably 96%, 97%, 98% or 99% identical to those above.

An additional embodiment of this aspect of the invention relates to a peptide or polypeptide which has the amino acid sequence of an epitope-bearing portion of a T1R-like ligand II polypeptide having an amino acid sequence described in (a), (b), (c), (d), or (e), above. Peptides or polypeptides having the amino acid sequence of an epitope-bearing portion of a T1R-like ligand II polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to a T1R-like ligand II polypeptide having an amino acid sequence described in (a), (b), (c), (d), or (e) above.

The invention also relates to fragments of the above-described polypeptides. Preferred polypeptide fragments according to the present invention include a polypeptide comprising: the mature polypeptide (amino acid residues from about 1 to about 203 in SEQ ID NO:2), the extracellular domain (amino acid residues from about 1 to about 168 in SEQ ID NO:2), the transmembrane domain (amino acid resdiues from about 169 to about 191 in SEQ ID NO:2), the intracellular domain (amino acid residues from about 191 to about 203 in SEQ ID NO:2), or the extracellular and intracellular domain with all or part of the transmembrane domain deleted.

It is believed that biological activities of the T1R-like ligand II of the present invention may be similar to the biological activities of the T1R ligand and IL-1. Significantly, higher or lower levels of T1R-like ligand II may be detected in tissues or bodily fluids (e.g., serum, plasma, urine, synovial fluid or spinal fluid) taken from an individual having a T1R ligand- or IL-1-related disorder, relative to a "normal" T1R-like ligand II gene expression level, i.e., the expression level in tissue or bodily fluids from an individual not having the T1R ligand- or IL-1-related disorder. Thus, detecting expression of T1R-like ligand II gene expression according to the present invention is a diagnostic marker.

In a further embodiment, the invention is related to a method for treating an individual in need of an increased or decreased level of T1R-like ligand II activity in the body, comprising administering to such an individual a composition comprising a T1R-like ligand II polypeptide or an inhibitor thereof The invention further provides methods for isolating antibodies that bind specifically to an T1R-like ligand II polypeptide having an amino acid sequence as described herein. Such antibodies may be useful diagnostically or therapeutically as described above.

BRIEF DESCRIPTION OF THE FIGURES

FIGS. 1A-B show the nucleotide (SEQ ID NO:1) and deduced amino acid (SEQ ID NO:2) sequences of the T1R-like ligand II protein determined by sequencing the cDNA clone contained in ATCC Deposit No. 97655. The protein has a leader sequence of about 26 amino acid residues (first underlined sequence), an extracellular mature domain of about 168 amino acid residues (sequence between the first and second underlined sequences), a transmembrane domain of about 23 amino acid residues (second underlined sequence), and an intracellular domain of about 12 amino acid residues (the remaining sequence).

FIG. 2 shows the regions of similarity between the amino acid sequences of the T1R-like ligand II and the protein sequence of GenBank accession No. U41804 (SEQ ID NO:3), showing an overall 56% identity.

DESCRIPTION OF THE INVENTION

Figure 3:
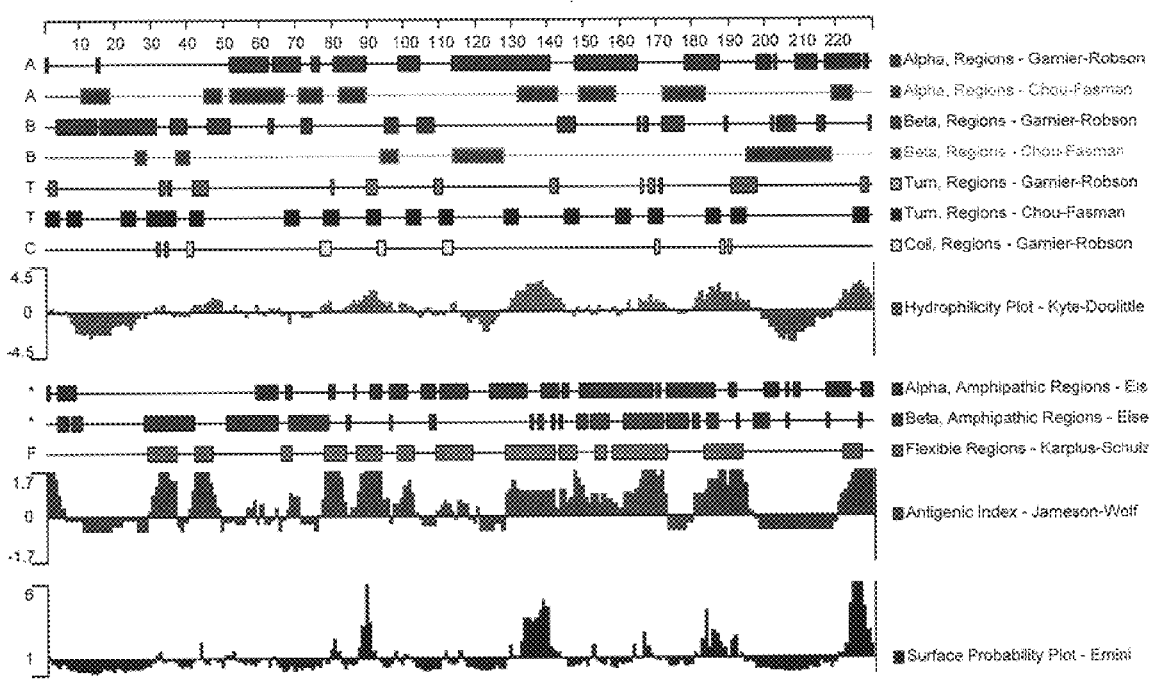
FIG. 3 provides an analysis of the T1R-like ligand II amino acid sequence. Alpha, beta, turn and coil regions; hydrophilicity and hydrophobicity; amphipathic regions; flexible regions; antigenic index and surface probability are shown.

The present invention provides an isolated nucleic acid molecule comprising a polynucleotide encoding a T1R-like ligand II protein having an amino acid sequence shown in FIGS. 1A-B (SEQ ID NO:2), which was determined by sequencing a cloned cDNA. The T1R-like ligand II protein of the present invention shares sequence homology with the T1R ligand (SEQ ID NO:3).

The nucleotide sequence in FIGS. 1A-B (SEQ ID NO:1) was obtained by sequencing the HE9BK24 clone, which was deposited on Jul. 12, 1996 at the American Type Culture Collection, 10801 University Boulevard, Manassas, Va. 20110–2209. and given accession number 97655. The deposited clone is contained in the pBluescript SK(–) plasmid (Stratagene, LaJolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of peptide, polypeptides or proteins encoded by DNA molecules determined herein were expected by translation of a DNA sequence determined as above. Therefore, as is known in the art for any DNA sequence determined by this automated approach, any nucleotide sequence determined herein can contain some errors. Nucleotide sequences determined by automation are typically at least about 90% identical, more typically at least about 95% to at least about 99.9% identical to the actual nucleotide sequence of the sequenced DNA molecule.

The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the expected amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence is replaced by the ribonucleotide uridine (U). For instance, reference to an RNA molecule having the sequence in SEQ ID NO:1 set forth using deoxyribonucleotide abbreviations is intended to indicate an RNA molecule having a sequence in which each deoxynucleotide A, G or C in SEQ ID NO:1 has been replaced by the corresponding ribonucleotide A, G or C, and each deoxynucleotide T has been replaced by a ribonucleotide U.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Using the information provided herein, such as the nucleotide sequence in FIGS. 1A-B (SEQ ID NO:1), a nucleic acid molecule of the present invention encoding an T1R-like ligand II polypeptide can be obtained using standard cloning and screening procedures, such as those for cloning cDNAs using mRNA as starting material. Illustrative of the invention, the nucleic acid molecule described in FIGS. 1A-B (SEQ ID NO:1) was discovered in a cDNA library derived from nine week old human embryo tissue. Further, the gene was also found in cDNA libraries derived from the following types of human cells: prostate, anergic T-cell, TF274 stromal, WI 38, Soares breast, and Soares placenta.

The T1R-like ligand II cDNA contains an open reading frame encoding a protein of about 229 amino acid residues whose initiation codon is at positions 55–57 of the nucleotide sequence shown in SEQ ID NO:1; a predicted leader sequence of about 26 amino acid residues and a deduced molecular weight of about 26 kDa. The amino acid sequence of the mature T1R-like ligand II protein is shown in SEQ ID NO:2 from amino acid residue 1 to residue 203. The mature T1R-like ligand II protein has three main structural domains. These include the extracellular domain, from amino acid residue about 1 to about 168 in SEQ ID NO:2; the transmembrane domain, from amino acid residue about 169 to about 191 in SEQ ID NO:2; and the intracellular domain, from amino acid residue about 192 to about 203 in SEQ ID NO:2. The T1R-like ligand II protein of the present invention in SEQ ID NO:2 is about 56% identical and about 75% similar to the T1R ligand, which can be accessed on GenBank as Accession No. U41804.

As indicated, the present invention also provides the mature form(s) of the T1R-like ligand II protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature T1R-like ligand II polypeptides having the amino acid sequence encoded by the cDNA clone contained in the host identified as ATCC Deposit No. 97655 and as shown in SEQ ID NO:2. By the mature T1R-like ligand II protein having the amino acid sequence encoded by the cDNA clone contained in the host identified as ATCC Deposit 97655 is meant the mature form(s) of the T1R-like ligand II protein produced by expression in a mammalian cell (e.g., COS cells, as described below) of the complete open reading frame encoded by the human DNA sequence of the clone contained in the vector in the deposited host. As indicated below, the mature T1R-like ligand II having the amino acid sequence encoded by the cDNA clone contained in ATCC Deposit No. 97655 may or may not differ from the predicted "mature" T1R-like ligand II protein shown in SEQ ID NO:2 (amino acids from about 1 to about 203) depending on the accuracy of the predicted cleavage site based on computer analysis.

Methods for predicting whether a protein has a secretory leader as well as the cleavage point for that leader sequence are available because it is known that much of the cleavage specificity for a secretory protein resides in certain amino acid residues within the signal sequence and the N-terminus of the mature protein, particularly residues immediately surrounding the cleavage site. For instance, the method of McGeoch (*Virus Res.* 3:271–286 (1985)) uses the information from a short N-terminal charged region and a subsequent uncharged region of the complete (uncleaved) protein. The method of von Heinje (*Nucleic Acids Res.* 14:4683–4690 (198)) uses the information from the residues surrounding the cleavage site, typically residues −13 to +2 where +1 indicates the amino acid terminus of the mature protein. The accuracy of predicting the cleavage points of known mammalian secretory proteins for each of these methods is in the range of 75–80%. von Heinje, supra. However, the two methods do not always produce the same predicted cleavage point(s) for a given protein.

As one of ordinary skill would appreciate, due to the possibilities of sequencing errors discussed above, as well as the variability of cleavage sites for leaders in different known proteins, the actual T1R-like ligand II encoded by the deposited cDNA comprises about 229 amino acids, but can be anywhere in the range of 215–245 amino acids; and the deduced leader sequence of this protein is about 26 amino acids, but can be anywhere in the range of about 15 to about 30 amino acids. Further, for example, the exact locations of the T1R-like ligand II protein extracellular, intracellular and transmembrane domains in SEQ ID NO:2 may vary slightly (e.g., the exact amino acid positions may differ by about 1 to about 5 residues compared to that shown in SEQ ID NO:2) depending on the criteria used to define the domain.

As indicated, nucleic acid molecules of the present invention can be in the form of RNA, such as mRNA, or in the form of DNA, including, for instance, cDNA and genomic DNA obtained by cloning or produced synthetically. The DNA can be double-stranded or single-stranded. Single-stranded DNA or RNA can be the coding strand, also known as the sense strand, or it can be the non-coding strand, also referred to as the anti-sense strand.

Isolated nucleic acid molecules of the present invention include DNA molecules comprising an open reading frame (ORF) with an initiation codon at positions 55–57 of the nucleotide sequence shown in FIGS. 1A-B (SEQ ID NO:1) and further include DNA molecules which comprise a sequence substantially different that all or part of the ORF whose initiation codon is at position 55–57 of the nucleotide sequence in FIGS. 1A-B (SEQ ID NO:1) but which, due to the degeneracy of the genetic code, still encode the T1R-like ligand II protein or a fragment thereof. Of course, the genetic code is well known in the art. Thus, it would be routine for one skilled in the art to generate the degenerate variants described above.

In another aspect, the invention provides isolated nucleic acid molecules encoding the T1R-like ligand II protein having an amino acid sequence encoded by the cDNA clone contained in the plasmid deposited as ATCC Deposit No. 97655 on Jul. 12, 1996. Preferably, this nucleic acid molecule will encode the mature polypeptide encoded by the above-described deposited cDNA clone.

The invention further provides an isolated nucleic acid molecule having the nucleotide sequence shown in FIGS. 1A-B (SEQ ID NO:1) or the nucleotide sequence of the T1R-like ligand II cDNA contained in the above-described deposited clone, or having a sequence complementary to one of the above sequences. Such isolated molecules, particularly DNA molecules, are useful as probes for gene mapping by in situ hybridization with chromosomes and for detecting expression of the T1R-like ligand II gene in human tissue, for instance, by Northern blot analysis. As described in detail below, detecting altered T1R-like ligand II gene expression in certain tissues may be indicative of certain disorders.

The present invention is further directed to fragments of the isolated nucleic acid molecules described herein. By a fragment of an isolated nucleic acid molecule having the nucleotide sequence of the deposited cDNA or the nucleotide sequence shown in FIGS. 1A-B (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 100, 150, 200, 250, 300, 350, 400, 450, 500, 500, 600, or 650 nt in length are also useful according to the present invention as are fragments corresponding to most, if not all, of the nucleotide sequence of the deposited cDNA or as shown in FIGS. 1A-B (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A-B (SEQ ID NO:1). Since the gene has been deposited and the nucleotide sequence shown in FIGS. 1A-B (SEQ ID NO:1) is provided, generating such DNA fragments would be routine to the skilled artisan. For example, restriction endonuclease cleavage or shearing by sonication could easily be used to generate fragments of various sizes. Alternatively, such fragments could be generated synthetically.

Preferred nucleic acid fragments-of the present invention include nucleic acid molecules encoding: a polypeptide comprising the T1R-like ligand II extracellular domain (amino acid residues from about 1 to about 168 in SEQ ID NO:2); a polypeptide comprising the T1R-like ligand It transmembrane domain (amino acid residues from about 169 to about 191 in SEQ ID NO:2); a polypeptide comprising the T1R-like ligand II intracellular domain (amino acid residues from about 192 to about 203 in SEQ ID NO:2); and a polypeptide comprising the T1R-like ligand II extracellular and intracellular domains having all or part of the transmembrane domain deleted. Further preferred nucleic acid fragments of the present invention include nucleic acid molecules encoding epitope-bearing portions of the T1R-like ligand II portion rotein. In particular, isolated nucleic acid molecules are provided encoding polypeptides comprising the following amino acid residues in SEQ ID NO:2, which the present inventors have determined are hydrophilic regions of the T1R-like ligand II protein: a polypeptide comprising amino acid residues from about 17 to about 26 in SEQ ID NO:2; a polypeptide comprising amino acid residues from about 56 to about 72 in SEQ ID NO:2; a polypeptide comprising amino acid residues from about 103 to about 120 in SEQ ID NO:2; a polypeptide comprising amino acid residues from about 136 to about 149 in SEQ ID NO:2; and a polypeptide comprising amino acid residues from about 155 to about 171 in SEQ ID NO:2. Methods for determining other such epitope-bearing portions of the T1R-like ligand II protein are described in detail below.

In addition, the present inventors have identified nucleic acid molecules having nucleotide sequences related to extensive portions of SEQ ID NO:1 which have been determined from the following related cDNA clone: HPVAA83R (SEQ ID NO:11).

The following public ESTs are related to extensive portions of SEQ ID NO:1: GenBank accession No. AA013099 (SEQ ID NO:12), GenBank accession No. AA251084 (SEQ ID NO:13), GenBank accession No. R58562 (SEQ ID NO:14), GenBank accession No. N28878 (SEQ ID NO:15), GenBank accession No. AA019348 (SEQ ID NO:16), GenBank accession No. N49615 (SEQ ID NO:17), GenBank accession No. AA112675 (SEQ ID NO:18), GenBank accession No. AA082161 (SEQ ID NO:19), GenBank accession No. H03613 (SEQ ID NO:20), GenBank accession No. R54717 (SEQ ID NO:21), GenBank accession No. H27167 (SEQ ID NO:22), GenBank accession No. AA188741 (SEQ ID NO:23), GenBank accession No. AA094735 (SEQ ID NO:24) and GenBank accession No. AA285143 (SEQ ID NO:25).

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 97655. By "stringent hybridization conditions" is intended overnight incubation at 42° C. in a solution comprising: 50% formamide, 5×SSC (750 mM NaCl, 75 mM trisodium citrate), 50 mM sodium phosphate (pH7.6), 5×Denhardt's solution, 10% dextran sulfate, and 20 μg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably at least about 30–70 nt of the reference polynucleotide. These are useful as diagnostic probes and primers as discussed above and in more detail below.

Of course, polynucleotides hybridizing to a larger portion of the reference polynucleotide (e.g., the deposited cDNA clone), for instance, a portion 100, 150, 200, 250, 300, 350, 400, 450, 500, 550, 600, or 650 nt in length, or even to the entire length of the reference polynucleotide, also are useful as probes according to the present invention, as are polynucleotides corresponding to most, if not all, of the nucleotide sequence of the deposited cDNA or the nucleotide sequence as shown in FIGS. 1A-B (SEQ ID NO:1). By a portion of a polynucleotide of "at least 20 nt in length," for example, is intended 20 or more contiguous nucleotides from the nucleotide sequence of the reference polynucleotide, (e.g., the deposited cDNA or the nucleotide sequence as shown in FIGS. 1A-B (SEQ ID NO:1)). As indicated, such portions are useful diagnostically either as a probe according to conventional DNA hybridization techniques or as primers for amplification of a target sequence by the polymerase chain reaction (PCR), as described, for instance, in Sambrook, J. et al., eds., *Molecular Cloning, A Laboratory Manual*, 2nd. edition, Cold Spring Harbor Laboratory Press, Cold Spring Harbor, N.Y. (1989).

Since an T1R-like ligand II cDNA clone has been deposited and its determined nucleotide sequence is provided in FIGS. 1A-B (SEQ ID NO:1), generating polynucleotides which hybridize to a portion of the T1R-like ligand II cDNA molecule would be routine to the skilled artisan. For example, restriction endonuclease cleavage or shearing by sonication of the T1R-like ligand II cDNA clone could easily be used to generate DNA portions of various sizes which are polynucleotides that hybridize to a portion of the T1R-like ligand II cDNA molecule. Alternatively, the hybridizing polynucleotides of the present invention could be generated synthetically according to known techniques.

Of course, a polynucleotide which hybridizes only to a poly A sequence (such as the 3' terminal poly(A) tract of the T1R-like ligand II cDNA shown in FIGS. 1A-B (SEQ ID NO:1)), or to a complementary stretch of T (or U) resides, would not be included in a polynucleotide of the invention used to hybridize to a portion of a nucleic acid of the invention, since such a polynucleotide would hybridize to any nucleic acid molecule contain a poly (A) stretch or the complement thereof (e.g., practically any double-stranded cDNA clone).

As indicated, nucleic acid molecules of the present invention which encode the T1R-like ligand II can include, but are not limited to, those encoding the amino acid sequence of the mature polypeptide, by itself, the coding sequence for the mature polypeptide and additional sequences, such as those encoding the about 26 amino acid leader sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, e.g., ribosome binding and stability of mRNA; an additional coding sequence which codes for additional amino acids, such as those which provide additional functionalities. Thus, the sequence encoding the polypeptide can be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are publicly and/or commercially available. As described in Gentz et al., *Proc. Natl. Acad Sci. USA* 86:821–824 (1989), for instance, hexa-histidine provides for convenient purification of the fusion protein. The "HA" tag is another peptide useful for purification which corresponds to an epitope derived from the influenza hemagglutinin (HA) protein, which has been described by Wilson et al., *Cell* 37:767 (1984). Other such fusion proteins include the T1R-like ligand II protein or a fragment thereof fused to Fc at the N- or C-terminus.

The present invention further relates to variants of the nucleic acid molecules of the present invention, which encode portions, analogs or derivatives of the T1R-like ligand II protein. Variants can occur naturally, such as a natural allelic variant. By an "allelic variant" is intended one of several alternate forms of a gene occupying a given locus on a chromosome of an organism. Non-naturally occurring variants can be produced, e.g., using art-known mutagenesis techniques.

Such variants include those produced by nucleotide substitutions, deletions or additions. The substitutions, deletions or additions can involve one or more nucleotides. The variants can be altered in coding or non-coding regions or both. Alterations in the coding regions can produce conservative or non-conservative amino acid substitutions, deletions or additions. Especially preferred among these are silent substitutions, additions and deletions, which do not alter the properties and activities of the T1R-like ligand II or portions thereof Also especially preferred in this regard are conservative substitutions.

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence at positions from about 1 to about 203 in SEQ ID NO:2; (d) a nucleotide sequence encoding the polypeptide having the amino acid sequence encoded by the cDNA clone contained in ATCC Deposit No. 97655; (e) a nucleotide sequence encoding the mature T1R-like ligand II polypeptide having the amino acid sequence encoded by the cDNA clone contained in ATCC Deposit No. 97655; or (f) a nucleotide sequence complementary to any of the nucleotide sequences in (a), (b), (c), (d), or (e).

By a polynucleotide having a nucleotide sequence at least, for example, 95% "identical" to a reference nucleotide sequence encoding a T1R-like ligand II polypeptide is intended that the nucleotide sequence of the polynucleotide is identical to the reference sequence except that the polynucleotide sequence can include up to five mutations per each 100 nucleotides of the reference nucleotide sequence encoding the T1R-like ligand II polypeptide. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence may be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular polypeptide is at least 95%, 96%, 97%, 98%, or 99% identical to, for instance, the amino acid sequence shown in FIGS. 1A-B (SEQ ID NO:2) or to the amino acid sequence encoded by deposited cDNA clone can be determined conventionally using known computer programs such the BESTFIT program (Wisconsin Sequence Analysis Package, Version 8 for Unix, Genetics Computer Group, University Research Park, 575 Science Drive, Madison, Wis. 53711. When using BESTFIT or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The present application is directed to nucleic acid molecules at least 95%, 96%, 97%, 98%, or 99% identical to a nucleic acid sequence described above irrespective of whether they encode a polypeptide having T1R-like ligand II protein activity. This is because, even where a particular nucleic acid molecule does not encode a polypeptide having T1R-like ligand II activity, one of skill in the art would still know how to use the nucleic acid molecule, for instance, as a hybridization probe or a polymerase chain reaction (PCR) primer. Uses of the nucleic acid molecules of the present invention that do not encode a polypeptide having T1R-like ligand It activity include, inter alia, (1) isolating the T1R-1 like ligand II gene or allelic variants thereof in a cDNA library; (2) in situ hybridization (e.g., "FISH") to metaphase chromosomal spreads to provide precise chromosomal location of the T1R-like ligand II gene as described in Verma et al., *Human Chromosomes: a Manual of Basic Techniques*, Pergamon Press, New York (1988); and (3) Northern Blot analysis for detecting T1R-like ligand II mRNA expression in specific tissues.

Preferred, however, are nucleic acid molecules having sequences at least 95%, 96%, 97%, 98%, or 99% identical to a nucleic acid sequence described above which do, in fact, encode a polypeptide having T1R-like ligand II protein activity.

By "a polypeptide having T1R-like ligand II rotein activity" is intended polypeptides exhibiting activity similar, but not necessarily identical, to an activity of the T1R-like ligand II protein of the invention as measured in a particular biological assay. T1R-like ligand II activity can be assayed using known receptor binding assays (Mitcham, J. L. et al., *J. Biol. Chem.* 271:5777–5783 (1996); and Gayle, M. A. et al., *J. Biol. Chem.* 271:5784–5789 (1996)). These assays include an NF-κB gel shift assay, an in vitro Thr-669 kinase assay, and an IL-8 pomoter activation assay.

To perform these assays, it is first necessary to transfect mammalian cells with an expression vector containing the cDNA for a suitable receptor. For example, an expression vector containing the cDNA for the T1/ST2 receptor can be used. This cDNA can be obtained as described (Klemenz, R. et al., *Proc, Natl. Acad. Sci. USA*. 86:5708–5712 (1989); Tominaga, S., *FEBS Lett.* 258:301–304; Bergers, G. et al., *EMBO J.* 13:117–1188)). Alternatively, T1/ST2 cDNA can be amplified using the polymerase chain reaction. A commercially available cDNA library, prepared from mRNA from a suitable tissue or cell type (such as NIH-3T3 cells (Klemenz, R. et al., *Proc, Nail. Acad. Sci. U.S.A.* 86:5708–5712 (1989)), can be used as template. Using any of several transfection methods well known to those of ordinary skill in the art, a suitable cell line (e.g., COS 7 cells) can be transfected with the T1/ST2 expression plasmid. Expression of the receptor can be verified by radioimmunoassay (see Mitcham, J. L. et al., *J. Biol. Chem.* 271:5777–5783 (1996)). One to three days post-transfection, confluent transfected COS7 cells are stimulated with 1–10 ng of T1R-like ligand II protein for 15 minutes to 20 hours. Duration of stimulation by T1R-like ligand II protein will vary, depending on which assay is used, and can be determined using only routine experimentation.

To perform the NF-κB assay, nuclear extracts from transfected cells are prepared immediately after stimulation (Ostrowski, J. et al., *J. Biol. Chem.* 266: 12722–12733 (1991)). A double-stranded synthetic oligonucleotide probe (5' TGACAGAGGGACTTTCCGAGAGGA 3'(SEQ ID NO:10)) containing the NF-κB enhancer element from the immunoglobulin κ light chain is 5'-end labeled by phosphorylation with [γ-$^{32}$ P]ATP. Nuclear extracts (10 μg) are incubated with radiolabeled probe for 20 minutes at room temperature, and protein-DNA complexes are resolved by electrophoresis in a 0.5×TBE, 10% polyacrylamide gel .

To perform the in vitro Thr-669 kinase assay, cytoplasmic extracts of transfected cells are prepared immediately after stimulation (Bird, T. A. et al., *Cytokine* 4:429–440 (1992)). 10μl of cell extract is added to 20μl of reaction mixture containing 20 mM HEPES buffer (pH 7.4), 15 mM MgCl$_2$, 15 μM ATP, 75μCi/ml [γ-$^{32}$P]ATP, and 750 μM substrate peptide (residues 663–673 of EGFR). Blanks are incubated with distilled H$_2$O in place of the peptide. After incubation at 30° C. for 20 minutes, the reactions are terminated by addition of formic acid. Reactions are cleared by centrifugation, and 30 μl of supernatant are spotted on phosphocellulose paper discs. After washing (three times with 75 mM orthophosphoric acid) and drying, peptide-incorporated counts are determined by monitoring Cerenkov counts. Results are expressed as the ratio of Thr-669 kinase activity detected in nonstimulated cells compared to activity detected in stimulated cells.

To perform the IL-8β pomoter activation assay, COS7 cells (1×10$^5$ cells per well in a multi-well tissue culture plate) are cotransfected with the T1/ST2 receptor expression vector and the pIL-8p reporter plasmid (Mitcham, J. L. et al., *J. Biol. Chem.* 271:5777–5783 (1996)). One day post-transfection, the medium is changed and cells are either stimulated with 1 ng/ml L-1α or are left stimulated. 12–16 hours post-stimulation, cells are washed twice with binding medium containing 5% (w/v) non-fat dry milk (5% MBM) and blocked with 2 ml of 5% MBM at room temperature for 30 minutes. Cells are then incubated at room temperature for 60–90 minutes with 1.5 ml/well of 5% MBM containing 1αμg/ml of an anti-IL-2Rα antibody (R&D Systems, Minneapolis, Minn.) with gentle rocking. Cells are washed once with 5% MBM and incubated with 1 ml/well of 5% MBM containing 1:100 dilution of $^{125}$I-goat anti-mouse IgG (Sigma, St. Louis, Mo.) for 60 minutes at room temperature. Wells are washed four times with 5% MBM and twice with phosphate-buffered saline. Wells are stripped by the addition of 1 ml of 0.5 M NaOH, and total counts are determined. Results are expressed as total cpm averaged over two duplicate or three triplicate wells.

Thus, "a polypeptide having T1R-like ligand II protein activity" includes polypeptides that exhibit T1R-like ligand II protein activity in at least one of the above-described assays.

Of course, due to the degeneracy of the genetic code, one of ordinary skill in the art will immediately recognize that a large number of the nucleic acid 785 molecules having a sequence at least 95%, 96%, 97%, 98%, or 99% identical to a nucleic acid sequence described above will encode a polypeptide "having T1R-like ligand II protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having T1R-like ligand II activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., *Science* 247:130–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U., et al., supra, and the references cited therein.

Vectors and Host Cells

The present invention also relates to vectors which include the isolated DNA molecules of the present invention, host cells which are genetically engineered with the recombinant vectors, and the production of T1R-like ligand II polypeptides or fragments thereof by recombinant techniques.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation.

The coding portion of the mature transcripts expressed by the constructs will include a translation initiating AUG at the beginning and a termination codon appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include bacterial cells, such as *E. coli*, Streptomyces and *Salmonella tphimurium* cells; fungal cells, such as yeast cells; insect cells such as Drosophila S2and Spodoptera Sf9 cells; animal cells such as CHO, COS and Bowes melanoma cells; and plant cells. Appropriate culture media and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; pSVK3, pBPV, pMSG and pSVL available from Pharmacia, and pA2 vailable from Qiagen. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-1 promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods in Molecular Biology* (198).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

Thus, the polypeptide may be expressed in a modified form, such as a fusion protein, and may include not only secretion signals but also additional heterologous functional regions. For instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL-5- has been fused with Fc portions for the purpose of high-throughput screening assays to identify antagonists of hIL-5. See, D. Bennett et al., *Journal of Molecular Recognition*, Vol. 8 52–58 (1995) and K. Johanson et al., *The Journal of Biological Chemistry*, Vol. 270, No. 16, pp 9459–9471 (1995).

The T1R-like ligand II can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Polypeptides and Peptides of the T1R-like Ligand II

The invention further provides an isolated T1R-like ligand II polypeptide having the amino acid sequence encoded by the deposited cDNA, or the amino acid sequence in FIGS. 1A-B (SEQ ID NO:2), or a peptide or polypeptide comprising a portion of the above polypeptides. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

By "isolated" polypeptide or protein is intended a polypeptide or protein removed from its native environment. For example, recombinantly produced polypeptides and proteins expressed in host cells are considered isolated for purposes of the invention as are native or recombinant polypeptides and proteins which have been substantially purified by any suitable technique such as, for example, the one-step method described in Smith and Johnson, *Gene* 67:31–40 (1988).

It will be recognized in the art that some amino acid sequence of the T1R-like ligand II can be varied without significant effect on the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the T1R-like ligand II which show substantial T1R-like ligand II activity or which include regions of T1R-like ligand II such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in *Protein Sequences: Tolerance to Amino Acid Substitutions*," *Science* 247:1306–1310 (1990).

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the T1R-like ligand II protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al., *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-$\alpha$ to only one of the two known types of TNF receptors. Thus, the T1R-like ligand II of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given PAPAI polypeptide will not be more than 50, 40, 30, 20, 10, 5, or 3.

Amino acids in the T1R-like ligand II protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al., *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or a native source. For example, a recombinantly produced version of the T1R-like ligand II polypeptide can be substantially purified by the one-step method described in Smith and Johnson, *Gene* 67:31–40 (1988).

The polypeptides of the present invention include the polypeptide encoded by the deposited cDNA including the leader; the mature polypeptide encoded by the deposited the cDNA minus the leader (i.e., the mature protein); a polypeptide comprising amino acids about -26 to about 203 in SEQ ID NO:2; a polypeptide comprising amino acids about -25 to about 203 in SEQ ID NO:2; a polypeptide comprising amino acids about 1 to about 203 in SEQ ID NO:2; as well as polypeptides at least 95% identical, and more preferably at least 96%, 97%, 98% or 99% identical to the polypeptide encoded by the deposited cDNA, to the polypeptide of SEQ ID NO:2, and also include portions of such polypeptides with at least 30 amino acids and more preferably at least 50 amino acids.

By a polypeptide having an amino acid sequence at least, for example, 95% "identical" to a reference amino acid sequence of a T1R-like ligand II polypeptide is intended that the amino acid sequence of the polypeptide is identical to the reference sequence except that the polypeptide sequence may include up to five amino acid alterations per each 100 amino acids of the reference amino acid sequence of the T1R-like ligand II polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in FIGS. 1A-B (SEQ ID NO:2) or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In another embodiment of the present invention, there are provided fragments of the polypeptides described herein. Preferred fragments include: the extracellular domain (amino acid residues from about 1 to about 168 in SEQ ID NO:2); the transmembrane domain (amino acid residues from about 169 to about 191 in SEQ ID NO:2); the intracellular domain (amino acid residues from about 191 to about 203 in SEQ ID NO:2); and the intracellular domain with all or part of the transmembrane domain deleted.

The polypeptide of the present invention could be used as a molecular weight marker on SDS-PAGE gels or on molecular sieve gel filtration columns using methods well known to those of skill in the art.

As described in detail below, the polypeptides of the present invention can be used to raise polyclonal and monoclonal antibodies, which are useful in diagnostic assays for detecting T1R-like ligand II expression as described below or as agonists and antagonists capable of enhancing or inhibiting T1R-like ligand II protein function. Further, such polypeptides can be used in the yeast two-hybrid system to "capture" T1R-like ligand II binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, H. M. et al., *Proc. Natl. Acad. Sci. USA* 81:3998–4002 (1984).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G. et al., *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes posttranslation processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson, I. A. et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides that can be used to generate T1R-like ligand II specific antibodies or fragments, include the following: a polypeptide comprising amino acid residues from about 17 to about 26 in SEQ ID NO:2; a polypeptide comprising amino acid residues from about 56 to about 72 in SEQ ID NO:2; a polypeptide comprising amino acid residues from about 103 to about 120 in SEQ ID NO:2; a polypeptide comprising amino acid residues from about 136 to about 149 in SEQ ID NO:2; and a polypeptide comprising amino acid residues from about 155 to about 171 in SEQ ID NO:2. As indicated above, the inventors have determined that the above polypeptide fragments are antigenic regions of the T1R-like II protein.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A., *Proc. Natl. Acad. Sci. USA* 82:5131–5135 (1985). This "Simultaneous Multiple Peptide Synthesis (SMPS)" process is further described in U.S. Pat. No. 4,631,211 to Houghten et al., (1968). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra;

Wilson et al., supra; Chow, M. et al., *Proc. Natl. Acad. Sci. USA* 82:910–914; and Bittle, F. J. et al., *J. Gen. Virol.* 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., (1984), supra, discloses a procedure for rapid concurrent synthesis on solid supports of hundreds of peptides of sufficient purity to react in an enzyme-liked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al., (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, T1R-like ligand II polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric T1R-like ligand II protein or protein fragment alone (Fountoulakis et al., *J. Biochem.* 270:3958–3964 (1995)).

T1R-like Ligand II Related Disorder Diagnosis

For T1R-like ligand II related disorders, it is believed that substantially altered (increased or decreased) levels of T1R-like ligand II gene expression can be detected in tissue or other cells or bodily fluids (e.g., sera, plasma, urine, synovial fluid or spinal fluid) taken from an individual having such a disorder, relative to a "standard" T1R-like ligand II gene expression level, that is, the T1R-like ligand II gene expression level in tissue or bodily fluids from an individual not having the disorder. Thus, the invention provides a diagnostic method useful during diagnosis of an T1R-like ligand II-related disorder, which involves measuring the expression level of the gene encoding the T1R-like ligand II in tissue or other cells or body fluid from an individual and comparing the measured gene expression level with a standard T1R-like ligand II gene expression level, whereby an increase or decrease in the gene expression level compared to the standard is indicative of an T1R-like ligand II related disorder.

T1R-like ligand II-related disorders are believed to include, but are not limited to, leukemia, lymphoma, arteriosclerosis, autoimmune diseases, inflammatory diseases, Alzheimer's disease, ophthalmic diseases, apoptosis, intrauterine growth retardation, preeclampsia, pemphigus and psoriasis.

By individual is intended mammalian individuals, preferably humans. By "measuring the expression level of the gene encoding the T1-like ligand II" is intended qualitatively or quantitatively measuring or estimating the level of the T1R-like ligand II protein or the level of the mRNA encoding the T1R-like ligand II protein in a first biological sample either directly (e.g., by determining or estimating absolute protein level or mRNA level) or relatively (e.g., by comparing to the T1R-like ligand II protein level or mRNA level in a second biological sample). Preferably, the T1R-like ligand II protein level or mRNA level in the first biological sample is measured or estimated and compared to a standard T1R-like ligand II protein level or mRNA level, the standard being taken from a second biological sample obtained from an individual not having the disorder or being determined by averaging levels from a population of individuals not having the disorder. As will be appreciated in the art, once a standard T1R-like ligand II protein level or mRNA level is known, it can be used repeatedly as a standard for comparison.

By "biological sample" is intended any biological sample obtained from an individual, body fluid, cell line, tissue culture, or other source which contains T1R-like ligand II protein or mRNA. As indicated, biological samples include body fluids (such as sera, plasma, urine, synovial fluid and spinal fluid) which contain secreted mature T1R-like ligand II, or tissue sources found to express T1R-like ligand II protein. Methods for obtaining tissue biopsies and body fluids from mammals are well known in the art. Where the biological sample is to include mRNA, a tissue biopsy is the preferred source.

Total cellular RNA can be isolated from a biological sample using any suitable technique such as the single-step guanidinium-thiocyanate-phenol-chloroform method described in Chomczynski and Sacchi, *Anal. Biochem.* 162:15–159 (1987). Levels of mRNA encoding an T1R-like ligand II are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. T1R-like ligand II cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., *Cell* 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the T1R-like ligand II). Northern blot analysis can be performed as described above.

Preferably, levels of mRNA encoding the T1R-like ligand II are assayed using the RT-PCR method described in Makino et al., *Technique* 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the T1R-like ligand II) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying T1R-like ligand II levels in a biological sample can occur using any art-known method. Preferred for assaying T1R-like ligand II levels in a biological sample are antibody-based techniques. For example, T1R-like ligand II expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of T1R-like ligand II for Western-blot or dot/slot assay (Jalkanen, M., et al., *J. Cell. Biol.* 101:976–985 (1985); Jalkanen, M., et al., *J. Cell. Biol.* 105:3087–3096 (1987)). In this technique, which is based on the use of cationic solid phases, quantitation of T1R-like ligand II can be accomplished using isolated T1R-like ligand II as a standard. This technique can also be applied to body fluids. With these samples, a molar concentration of T1R-like ligand II will aid to set standard values of T1R-like ligand II content for different body fluids, like serum, plasma, urine, synovial fluid, spinal fluid, etc. The normal appearance of T1R-like ligand II amounts can then be set using values from healthy individuals, which can be compared to those obtained from a test subject.

Other antibody-based methods useful for detecting T1R-like ligand II levels include immunoassays, such as the enzyme linked immunosorbent assay (ELISA) and the radioimmunoassay (RIA). For example, T1R-like ligand II-specific monoclonal antibodies can be used both as an immunoadsorbent and as an enzyme-lebeled probe to detect and quantify the T1R-like ligand II. The amount of T1R-like ligand II present in the sample can be calculated by reference to the amount present in a standard preparation using a linear regression computer algorithm. Such an ELISA for detecting a tumor antigen is described in Iacobelli et al., *Breast Cancer Research and Treatment* 11:19–30 (1988). In another ELISA assay, two distinct specific monoclonal antibodies can be used to detect T1R-like ligand II in a body fluid. In this assay, one of the antibodies is used as the immunoadsorbent and the other as the enzyme-labeled probe.

The above techniques may be conducted essentially as a "one-step" or "two-step" assay. The "one-step" assay involves contacting T1R-like ligand II with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzymelabeled antibody/substrate reaction. Besides enzymes, other suitable labels include radioisotopes, such as iodine ($^{125}$I , $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying T1R-like ligand II levels in a biological sample obtained from an individual, T1R-like ligand II can also be detected in vivo by imaging. Antibody labels or markers for in vivo imaging of T1R-like ligand II include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A T1R-like ligand II-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for a disorder. It will be understood in the art that the size of the subject and the imaging system used will determine the quantity of imaging moieties needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain T1R-like ligand II. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, Burchiel, S. W. and Rhodes, B. A. eds., Masson Publishing Inc., (1982)).

T1R-like ligand II specific antibodies for use in the present invention can be raised against the intact T1R-like ligand II or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to T1R-like ligand II. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:31–325 (1983)). Thus, these portions are preferred.

The antibodies of the present invention may be prepared by any of a variety of methods. For example, cells expressing the T1R-like ligand II or an antigenic fragment thereof can be administered to an animal in order to induce the production of sera containing polyclonal antibodies. In a preferred method, a preparation of T1R-like ligand II protein is prepared and purified as described above to render it substantially free of natural contaminants. Such a preparation is then introduced into an animal in order to produce polyclonal antisera of greater specific activity.

In the most preferred method, the antibodies of the present invention are monoclonal antibodies (or T1R-like ligand II binding fragments thereof). Such monoclonal antibodies can be prepared using hybridoma technology (Colligan, *Current Protocols in Immunology*, Wiley Interscience, New York (1990–1996); Harlow & Lane, Antibodies: A Laboratory Manual, Cold Spring Harbor *Press, Cold Spring Harbor, N.Y.* (1988), Chapters 6–9, *Current Protocols in Molecular Biology*, Ausubel, infra, Chapter 11, entirely incorporated herein by reference). In general, such procedures involve immunizing an animal (preferably a mouse) with an T1R-like ligand II antigen or, more preferably, with an T1R-like ligand II-expressing cell. Suitable cells can be recognized by their capacity to bind anti-T1R-like ligand II antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 $\mu$g/l of nonessential amino acids, about 1,000 U/ml of penicillin, and about 100 $\mu$g/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection (ATCC) (Rockville, Md., USA). After fusion, the resulting hybridoma cells are selectively maintained in HAT medium, and then cloned by limiting dilution as described by Wands et al., *Gastroenterology* 80:225–232 (1981); Harlow & Lane, infra, Chapter 7. The hybridoma cells obtained through such a selection are then assayed to identify clones which secrete antibodies capable of binding the T 1 R-like ligand II antigen.

Alternatively, additional antibodies capable of binding to the T1R-like ligand II antigen may be produced in a two-step procedure through the use of anti-idiotypic antibodies. Such a method makes use of the fact that antibodies are themselves antigens, and therefore it is possible to obtain an antibody which binds to a second antibody. In accordance with this method, T1R-like ligand II specific antibodies are used to immunize an animal, preferably a mouse. The splenocytes of such an animal are then used to produce hybridoma cells, and the hybridoma cells are screened to identify clones which produce an antibody whose ability to bind to the T1R-like ligand II-specific antibody can be blocked by the T1R-like ligand II antigen. Such antibodies comprise anti-idiotypic antibodies to the T1R-like ligand II-specific antibody and can be used to immunize an animal to induce formation of further T1R-like ligand II-specific antibodies.

It will be appreciated that Fab and F(ab')$_2$ nd other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, T1R-like ligand II-binding fragments can be produced through the application of recombinant DNA technology or through synthetic chemistry.

Where in vivo imaging is used to detect enhanced levels of T1R-like ligand II for diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).

Further suitable labels for the T1R-like ligand II-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47Sc}$, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins et al., Eur. J. Nucl. Med. 10:29614 301 (1985); Carasquillo et al., J. Nucl. Med. 28:281–287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861–870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescarnine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and Fe.

Typical techniques for binding the above-described labels to antibodies are provided by Kennedy et al., (Clin. Chim. Acta 70:1–31 (197)), and Schurs et al., (Clin. Chim. Acta 81:1–40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of an T1R-like ligand II gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 nd 500 potential causative genes. (This assumes 1 megabase mapping resolution and one gene per 20 kb).

Treatment of T1R-like Ligand II Disorders

It is believed by the present inventors that T1R-like ligand II polypeptides of the present invention share biological activities with interleukin-1 (IL-1) and the T1R ligand. Thus, the T1R-like ligand II (particularly the mature form) can be exogenously added to cells, tissues, or the body of an individual to produce a therapeutic effect. In particular, disorders caused by a decrease in the standard level of T1R-like ligand II protein activity can be treated by administering an effective amount of a T1R-like ligand II polypeptide of the invention. Preferably, a pharmaceutical composition is administered comprising an amount of an isolated T1R-like ligand II polypeptide of the invention effective to increase the T1R-like ligand II protein activity. Disorders where such a therapy would likely be effective are discussed above and below.

One of ordinary skill will appreciate that effective amounts of a T1R-like ligand II polypeptide can be determined empirically for each condition where administration of a such a polypeptide is indicated. The polypeptide having T1R-like ligand II activity can be administered in pharmaceutical compositions in combination with one or more pharmaceutically acceptable carriers, diluents and/or excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition an other agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts.

The T1R-like ligand II composition to be used in the therapy will also be formulated and dosed in a fashion consistent with good medical practice, taking into account the clinical condition of the individual patient (especially the side effects of treatment with T1R-like ligand II alone), the site of delivery of the T1R-like ligand II composition, the method of administration, the scheduling of administration, and other factors known to practitioners. An "effective amount" of a T1R-like ligand II polypeptide for purposes herein is thus determined by such considerations.

As a general proposition, the total pharmaceutically effective amount of a T1R-like ligand II polypeptide administered parenterally per dose will be in the range of about 0.01 ng/kg/day to 10 μg/kg/day of patient body weight, although, as noted above, this will be subject to therapeutic discretion. More preferably, this dose is at least 1.0 ng/kg/day, and most preferably for humans between about 1.0 to 100 ng/kg/day for the hormone. If given continuously, the T1R-like ligand II is typically administered at a dose rate of about 0.01 ng/kg/hour to about 100 ng/kg/hour, either by 1–4 injections per day or by continuous subcutaneous infusions, for example, using a mini-pump. An intravenous bag solution may also be employed.

A course of T1R-like ligand II polypeptide treatment to affect the immune system appears to be optimal if continued longer than a certain minimum number of days, 7 days in the case of the mice. The length of treatment needed to observe changes and the interval following treatment for responses to occur appears to vary depending on the desired effect.

The T1R-like ligand II polypeptide is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,9196, EP 58,481), copolymers of L-glutamic acid and gamma-ethyl-L-glutamate (U. Sidman et al., *Biopolymers* 22:547–556 (1983)), poly(2-hydroxyethl methacrylate) (R. Langer et al., *J. Biomed. Mater. Res.* 15:167–277 (1981), and R. Langer, Chem. Tech. 12:98–105 (1982)), ethylene vinyl acetate (R. Langer et al., Id.) or poly-D-(–)-3-hydroxybutyric acid (EP 133,988). Sustained-release T1R-like ligand II compositions also include a liposomally entrapped T1R-like ligand II polypeptide. Liposomes containing a T1R-like ligand II polypeptide are prepared by methods known per se: DE 3,218,121; Epstein, et al., *Proc. Natl. Acad Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese Pat. Appl. 83-118008; U.S. Pat. Nos 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal T1R-like ligand II therapy.

For parenteral administration, in one embodiment, the T1R-like ligand II polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the T1R-like ligand II polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The T1R-like ligand II is typically formulated in such vehicles at a concentration of about 0.001 ng/ml to 500 ng/ml, preferably 0.1–10 ng/ml, at a pH of about 3 to 8. It will be understood that the use of certain of the foregoing excipients, carriers, or stabilizers will result in the formation of T1R-like ligand II salts.

T1R-like ligand II to be used for therapeutic administration must be sterile. Sterility is readily accomplished by filtration through sterile filtration membranes (e.g., 0.2 micron membranes). Therapeutic T1R-like ligand II compositions generally are placed into a container having a sterile access port, for example, an intravenous solution bag or vial having a stopper pierceable by a hypodermic injection needle.

T1R-like ligand II ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous T1R-like ligand II solution, and the resulting mixture is lyophilized. The infusion solution is prepared by reconstituting the lyophilized T1R-like ligand II using bacteriostatic Water-for-Injection.

For example, satisfactory results are obtained by oral administration of a polypeptide having T1R-like ligand II activity in dosages on the order of from 0.05 to 5000 ng/kg/day, preferably 0.1 to 1000 ng/kg/day, more preferably 10 to 100 ng/kg/day, administered once or, in divided doses, 1 to 4 times per day. On administration parenterally, for example by i.v. drip or infusion, dosages on the order of from 0.01 to 500 ng/kg/day, preferably 0.05 to 100 ng/kg/day and more preferably 0.1 to 50 ng/kg/day can be used. Suitable daily dosages for patients are thus on the order of from 2.5 ng to 250 μg p.o., preferably 5 ng to 50 μg p.o., more preferably 50 ng to 12.5 μg p.o., or on the order of from 0.5 ng to 25 μg i.v., preferably 2.5 ng to 500 μg i.v. and more preferably 5 ng to 2.5 μg i.v.

T1R-like Ligand II Antibody Therapy

By the invention, disorders caused by enhanced levels of T1R-like ligand II protein activity can be treated by administering an effective amount of an antagonist of a T1R-like ligand II polypeptide of the invention. Therefore, antibodies (preferably monoclonal) or antibody fragments that bind a T1R-like ligand II polypeptide of the present invention are useful in treating T1R-like ligand II-related disorders as are soluble T1R-like ligand II proteins, such as the extracellular domain, which competes with the intact protein for binding to the T1R-like ligand II receptor. Such antibodies and/or soluble T1R-like ligand II proteins are preferably provided in pharmaceutically acceptable compositions.

The pharmaceutical compositions of the present invention may be administered, for example, by the parenteral, subcutaneous, intravenous, intramuscular, intraperitoneal, transdermal, or buccal routes. Alternatively, or concurrently, administration may be oral. The dosage administered will be dependent upon the age, health, and weight of the recipient, kind of concurrent treatment, if any, frequency of treatment, and the nature of the effect desired.

Compositions within the scope of this invention include all compositions wherein the antibody, fragment or derivative is contained in an amount effective to achieve its intended purpose. While individual needs vary, determination of optimal ranges of effective amounts of each component is within the skill of the art. The effective dose is a function of the individual chimeric or monoclonal antibody, the presence and nature of a conjugated therapeutic agent (see below), the patient and his clinical status, and can vary from about 10 ng/kg body weight to about 100 mg/kg body weight. The preferred dosages comprise 0.1 to 10 mg/kg body wt.

Preparations of an T1R-like ligand II antibody or fragment for parenteral administration, such as in detectably labeled form for imaging or in a free or conjugated form for therapy, include sterile aqueous or non-aqueous solutions, suspensions, and emulsions. Examples of non-aqueous solvents are propyleneglycol, polyethyleneglycol, vegetable oil such as olive oil, and injectable organic esters such as ethyloleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, such as those based on Ringer's dextrose, and the like. Preservatives and other additives may also be present, such as, for example, antimicrobials, anti-oxidants, chelating agents, and inert gases and the like. See, generally, *Remington's Pharmaceutical Science*, 16th ed., Mack Publishing Co., Easton, Pa., 1980.

The antibodies described herein may be advantageously utilized in combination with other monoclonal or chimeric antibodies, or with lymphokines or hemopoietic growth factors, etc., which serve to increase the number or activity of effector cells which interact with the antibodies.

Expected Pleiotropic Biologic Effects of T1R-like Ligand II

The T1R-like ligand II polypeptides of the present invention are expected to have pleiotropic biological effects including many of those shown in Table 1 below. Similar biological effects have been shown for IL-1, particularly those associated with pancreatic endocrine tissue (Mandrup-Poulsen, T., et al., *Cytokine* 5:185 (1993)), thyroid glands (Rasmussen, A. K., Autoimmunity 16:141 (1993)), hypothalamic-pituitary-adrenal axis (Fantuzzi, G., & Ghezzi, P., *Mediator Inflamm*. 2:263 (1993); Rivier, C., *Ann. NY Acad. Sci.* 697:97 (1993); Rivier, C., & Rivest, S., *Ciba. Found. Symp.* 172:204 (1993)), fever (Coceani, F., "Fever: Basic Mechanisms and Management", New York, N.Y., Raven (1991) p. 59), bone metabolism (Tatakis, D. N., *J. Peridontol* 64:416 (1993)), destruction of cartilage in the pathogenesis of rheumatoid arthritis (Arend, W. P., & Dayer, J. M., *Arthritis Rheum* 33:305 (1990); Krane, S. M., et al., *Ann. NY Acad. Sci.* 580:340 (1990)), uterine implantation (Lewis, M. P., et al., *Placenta* 15:13 (1994)), and loss of lean body mass (Roubenoff, R., et al., *J. Clin. Invest.* 93:2379 (1994)).

TABLE 1

Possible Biologic Effects of T1R-like ligand II

Effects of systemically injected T1R-like ligand II

Fever; increased slow wave sleep; social depression; anorexia
Hypotension; myocardial suppression; tachycardia; lactic acidosis
Increased circulating nitric oxide; hypoaminoacidemia
Hyperinsulinemia; hyperglycemia; hypoglycemia
Stimulation of hypothalamic-pituitary-adrenal axis
Release of hypothalamic monoamines and neuropeptides
Neutrophilia; increased marrow cellularity; increased platelets
Increased hepatic acute phase protein synthesis
Hypoferremia; hypozincemia; increased sodium excretion
Hyperlipidemia; increased muscle protein breakdown
Hypoalbuminemia; decreased drug metabolism
Increased metastases
Increased nonspecific resistance to infection (pretreatment)
Learning defects in offspring after maternal IL-1 treatment
Effects of locally injected T1R-like ligand II Infiltration of neutrophils into rabbits knee joint
Increased proteoglycan breakdown in rabbit knee joint
Induction of uveitis following intravitreal injection TABLE 1-continued

| Possible Biologic Effects of T1R-like ligand II |
|---|
| Angiogenesis in anterior chamber of eye |
| Cellular infiltrate and cytokine induction in cerebral ventricles |
| Neutrophil and albumin influx into lungs after intratracheal instillation |
| Changes in immunologic responses |
| Increased antibody production (adjuvant effect) |
| Increased lymphokine synthesis (IL-2, -3, -4, -5, -6, -7, -10 and -12) |
| Increased IL-2 (β) receptor |
| Development of type 2 human T-cell clones |
| Inhibition of tolerance to protein antigens |
| Enhancement of spleen cell mitogenic response to LPS |
| Effects of T1R-like ligand II on cultured cells or tissues |
| Increased expression of ELAM-1, VCAM-1, ICAM-1 |
| Cytotoxicity (apoptosis) of insulin-producing islet β cells |
| Inhibition of thyroglobulin synthesis in thyrocytes |
| Cartilage breakdown, release of calcium from bone |
| Increased release of arachidonic acid, prostanoids, and eicosanoids |
| Increased mucus production and chloride flux in intestinal cells |
| Enhancement in chloride flux (GABAA receptor) in brain synaptosomes |
| Proliferation of fibroblasts, smooth muscle cells, messangial cells |
| Growth inhibition of hair follicles |
| Increased corticosterone synthesis by adrenals |

Assays used: pancreatic endocrine tissue (Mandrup-Poulsen, T., et al., Cytokine 5:185 (1993)), thyroid gland (Rasmussen, A. K., Autoimmunity 16:141 (1993)), hypothalamic-pituitary-adrenal axis (Fantuzzi, G., & Ghezzi, P., Mediator Inflamm. 2:263 (1993); Rivier, C., *Ann. NY Acad. Sci.* 697:97 (1993); Rivier, C., & Rivest, S., Ciba. Found. Symp. 172:204 (1993)), fever (Coceani, F., "Fever: Basic Mechanisms and Management", New York, N.Y., Raven (1991) p. 596), bone metabolism (Tatakis, D. N., *J. Peridontol* 64:416 (1993)), destruction of cartilage in the pathogenesis of rheumatoid arthritis (Arend, W. P., & Dayer, J. M., *Arthritis Rheum* 33:305 (1990); Krane, S. M., et al., *Ann. NY Acad Sci.* 580:340 (1990)), uterine implantation (Lewis, M. P., et al., *Placenta* 15:13 (1994)), and loss of lean body mass (Roubenoff, R., et al., *J. Clin. Invest.* 93:2379 (1994).

Having generally described the invention, the same will be more readily understood by reference to the following examples, which are provided by way of illustration and are not intended as limiting.

EXAMPLES

Example 1

Expression and Purification of T1R-like Ligand II in *E. coli*

The DNA sequence encoding the mature, extracellular soluble portion of T1R-like ligand II in the deposited cDNA clone is amplified using PCR oligonucleotide primers specific to the amino terminal sequences of the T1R-like ligand II and to vector sequences 3' to the gene. Additional nucleotides containing restriction sites to facilitate cloning are added to the 5' and 3' sequences respectively.

One of ordinary skill in the art will understand that the full-length, mature T1R-like ligand II protein (amino acid about 1 to about 203 in SEQ ID NO:2) can be expressed in *E. coli* using suitable 5' and 3' oligonucleotide primers.

The cDNA sequence encoding the extracellular domain of the full length T1R-like ligand II in the deposited clone is amplified using PCR oligonucleotide primers corresponding to the 5' and 3' sequences of the gene. The 5' primer contains the sequence 5'CGC <u>CCA TGG</u> CCG GCT TCA CAC CTT CC 3'(SEQ ID NO:4) containing the underlined Nco I site and 17 nucleotides (nucleotides 131–147) of the T1R-like ligand II protein coding sequence in FIGS. 1A-B (SEQ ID NO:1) beginning immediately after the signal peptide.

The 3' primer has the sequence 5'CGC <u>AAG CTT</u> TCA TCT ATC AAA GTT GCT TTC 3'(SEQ ID NO:5) containing a Hind III restriction site followed by a stop codon and 18 nucleotides reverse and complementary to nucleotides 619–636 of the T1R-like ligand II protein coding sequence in FIGS. 1A-B (SEQ ID NO:1).

The restriction sites are convenient to restriction enzyme sites in the bacterial expression vector pQE60, which are used for bacterial expression in M15/rep4 host cells in these examples. (Qiagen, Inc., Chatsworth, Calif., 91311). pQE60 encodes ampicillin antibiotic resistance ("$Amp^r$") and contains a bacterial origin of replication ("ori"), an IPTG inducible promoter, a ribosome binding site ("RBS"), a 6-His tag and restriction enzyme sites.

The amplified T1R-like ligand II DNA and the vector pQE60 both are digested with Nco I and Hind III and the digested DNAs are then ligated together. Insertion of the T1R-like ligand II DNA into the restricted pQE60 vector placed the T1R-like ligand II coding region downstream of and operably linked to the vector's IPTG-inducible promoter and in-frame with an initiating AUG appropriately positioned for translation of T1R-like ligand II.

The ligation mixture is transformed into competent *E. coli* cells using standard procedures. Such procedures are described in Sambrook et al., *Molecular Cloning: A Laboratory Manual*, 2 nd Ed.; Cold Spring Harbor Laboratory Press, Cold Spring Harbor, N.Y. (19896). *E coli* strain M15/rep4, containing multiple copies of the plasmid pREP4, which expresses lac repressor and confers kanamycin resistance ("$Kan^r$"), is used in carrying out the illustrative example described here. This strain, which is only one of many that are suitable for expressing T1R-like ligand II, is available commercially from Qiagen.

Transformants are identified by their ability to grow on LB plates in the presence of ampicillin and kanamycin. Plasmid DNA is isolated from resistant colonies and the identity of the cloned DNA was confirmed by restriction analysis.

Clones containing the desired constructs are grown overnight ("O/N") in liquid culture in LB media supplemented with both ampicillin (100 μg/ml) and kanamycin (25 μg/m).

The O/N culture is used to inoculate a large culture, at a dilution of approximately 1:100 to 1:250. The cells are grown to an optical density at 600nm ("OD600") of between 0.4 nd 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2×phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2×PBS.

Analysis of the preparation by standard methods of polyacrylamide gel electrophoresis reveals that the preparation contains about 95% monomer T1R-like ligand II having the expected molecular weight of approximately 26 kDa.

Example 2

Cloning and Expression of T1R-like Ligand II in a Baculovirus Expression System The cDNA sequence encoding the full length T1R-like ligand II in the deposited clone is amplified using PCR oligonucleotide primers corresponding to the 5' and 3' sequences of the gene:

The 5' primer has the sequence 5'CGC GGA TCC GCC ATC ATG GGC GAC AAG ATC TGG 3'(SEQ ID NO:6) containing the underlined BamHI restriction enzyme site followed by 18 nucleotides (nucleotides 55 to 72) of the sequence of the T1R-like ligand II protein in FIGS. 1A-B (SEQ ID NO:1). Inserted into an expression vector, as described below, the 5' end of the amplified fragment encoding T1R-like ligand II provides an efficient signal peptide. An efficient signal for initiation of translation in eukaryotic cells, as described by Kozak, M., *J. Mol. Biol.* 196:947–950 (1987) is appropriately located in the vector portion of the construct.

The 3' primer has the sequence 5'CGC GGT ACC TCA CAA TGT TAC GTA CTC TAG 3'(SEQ ID NO:7) containing the underlined Asp 718 restriction site followed by a stop codon and 18 nucleotides reverse and complementary to nucleotides 754–771 of the T1R-like ligand II coding sequence set out in FIGS. 1A-B (SEQ ID NO:1).

The cDNA sequence encoding the extracellular domain of the full length T1R-like ligand II in the deposited clone is amplified using PCR oligonucleotide primers corresponding to the 5' and 3' sequences of the gene:

The 5' primer has the sequence 5'CGC GGA TCC GCC ATC ATG GGC GAC AAG ATC TGG 3'(SEQ ID NO:6) containing the underlined BamHI restriction enzyme site followed by 18 nucleotides (nucleotides 55–72) of the sequence encoding the T1R-like ligand II protein set out in FIGS. 1A-B (SEQ ID NO:1). Inserted into an expression vector, as described below, the 5' end of the amplified fragment encoding T1R-like ligand II provides an efficient signal peptide. An efficient signal for initiation of translation in eukaryotic cells, as described by Kozak, M., *J. Mol Biol.* 196: 947–950 (1987) is appropriately located in the vector portion of the construct.

The 3' primer has the sequence 5'CGC GGT ACC TCA TCT ATC AAA GTT GCT TTC 3'(SEQ ID NO:8) containing the underlined Asp 718 restriction site followed by a stop codon and 18 nucleotides complementary and reverse to nucleotides 619–636 of the T1R-like ligand II coding sequence set out in FIGS. 1A-B (SEQ ID NO:i1).

The amplified fragment is isolated from a 1% agarose gel using a commercially available kit ("Geneclean," BIO 101 Inc., La Jolla, Calif.). The fragment then is digested with BamHI and Asp 718 nd again is purified on a 1% agarose gel. This fragment is designated herein F2.

The vector pA2 is used to express the T1R-like ligand II full length and extracellular domains of an T1R-like ligand II in the baculovirus expression system, using standard methods, as described in Summers et al., *A Manual of Methods for Baculovirus Vectors and Insect Cell Culture Procedures*, Texas Agricultural Experimental Station Bulletin No. 1555 (1987). The pA2 vector does not contain a signal peptide coding region. Thus, the T1R-like ligand II signal peptide is relied upon (nucleotides 55–132 in SEQ ID NO:1; amino acids −26 to −1 SEQ ID NO:2).

If the T1R-like ligand II signal peptide does not result in efficient expression of the T1R-like ligand II protein, the pA2-GP vector may be used instead of the pA2 vector. The signal peptide of AcMNPV gp67, including the N-terminal methionine, is located just upstream of a BamHI site. One of ordinary skill in the art will understand that if the pA2-GP expression vector is used, the 5' oligonucleotide used should not contain sequence coding for the T1R-like ligand II signal peptide. Instead, the 5' oligonucleotide should begin at nucleotide 131.

Both the pA2 nd pA2-GP expression vectors contain the strong polyhedrin promoter of the *Autographa californica* nuclear polyhedrosis virus (AcMNPV) followed by convenient restriction sites. The polyadenylation site of the simian virus 40 ("SV40") is used for efficient polyadenylation. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2 or pA2-GP, such as pAc373, pVL-941 nd pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virolog* 170:31–39, among others.

The plasmid is digested with the restriction enzyme BamHI and Asp 718 and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2re ligated together with T4 DNA ligase. *E. coil* HB 101 cells are transformed with ligation mix and spread on culture plates. Bacteria are identified that contain the plasmid with the human T1R-like ligand II gene by digesting DNA from individual colonies using BamHI and Asp 718 and then analyzing the digestion product by gel electrophoresis. The sequence of the cloned fragment is confirmed by DNA sequencing. This plasmid is designated herein pBacT1R-like ligand II.

5 µg of the plasmid pBacT1R-like ligand II is co-transfected with 1.0 µg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84: 7413–7417 (1987). 1 µg of BaculoGold™ virus DNA and 5 µg of the plasmid pBacT1R-like ligand II are mixed in a sterile well of a microtiter plate containing 50 µl of serum-free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal"(Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. Clones containing properly inserted T1R-like ligand II re identified by DNA analysis including restriction mapping and sequencing. This is designated herein as V-T1R-like ligand II.

Sf9 cells are grown in Grace's medium supplemented with 10% heat-inactivated FBS. The cells are infected with the recombinant baculovirus V-T1R-like ligand II at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 µCi of $^{35}$S-methionine and 5 µCi $^{35}$S-cysteine (available from Amersham) are added. The cells are further incubated for 16 hours and then they are harvested by centrifugation, lysed and the labeled proteins are visualized by SDS-PAGE and autoradiography.

Example 3

Cloning and Expression in Mammalian Cells

Most of the vectors used for the transient expression of the T1R-like ligand II protein gene sequence in mammalian cells should carry the SV40 origin of replication. This allows the replication of the vector to high copy numbers in cells (e.g. COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g. RSV, HTLV-I, HIV-I and the early promoter of the cytomegalovirus (CMV). However, cellular signals can also be used (e.g. human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 671096). Mammalian host cells that could be used include, human Hela, 283, H9and Jurkat cells, mouse NIH3T3 and C127 cells, Cos 1, Cos 7 and CV1, African green monkey cells, quail QC1–3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., Biochem J. 227:277–279 (1991); Bebbington et al., Bio/Technology 10:169–175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., Molecular and Cellular Biology, 438–4470 (March, 1985)) plus a fragment of the CMV-enhancer (Boshart et al., Cell 41:521–530 (1985)). Multiple cloning sites, e.g. with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

An expression plasmid is made by cloning a cDNA encoding T1R-like ligand II into the expression vector pcDNAI/Amp (which can be obtained from Invitrogen, Inc.).

The expression vector pcDNAI/amp contains: (Dower, Colotta, F., et al., *Immunol Today* 15:562 (1994)) an *E.coli* origin of replication effective for propagation in *E. coli* and other prokaryotic cells; (Greenfeder, S. A. , et al., *J. Biol. Chem.* 270:13757 (1995)) an ampicillin resistance gene for selection of plasmid-containing prokaryotic cells; (Polan, M. L., et al., *Am. J. Obstet. Gynecol.* 170:1000 (1994)) an SV40 origin of replication for propagation in eukaryotic cells; (Carinci, Mora, M., et al., *Prog. Clin. Biol. Res.* 349:205 (1990)) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire T1R-like ligand II precursor and an HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37:767 (1984). The fusion of the HA tag to the target protein allows easy detection of the recombinant protein with an antibody that recognizes the HA epitope.

The plasmid construction strategy is as follows.

The T1R-like ligand II cDNA of the deposited clone is amplified using primers that contain convenient restriction sites, much as described above regarding the construction of expression vectors for expression of T1R-like ligand II in *E coli*. To facilitate detection, purification and characterization of the expressed T1R-like ligand II, one of the primers contains a hemagglutinin tag ("HA tag") as described above.

One of ordinary skill in the art will understand that the full-length T1R-like ligand II protein (amino acid about −26 to about 203 in SEQ ID NO:2) can be expressed in COS cells using suitable 5' and 3' oligonucleotide primers.

The cDNA sequence encoding the extracellular domain of the full length T1R-like ligand II in the deposited clone is amplified using PCR oligonucleotide primers corresponding to the 5' and 3' sequences of the gene. The 5' primer has the following sequence:

5'CGC GGA TCC GCC ATC ATG GGC GAC AAG ATC TGG 3'(SEQ ID NO:6), containing the underlined BamH1 site and 18 nucleotides (nucleotides 55 to 72) of the T1R-like ligand II coding sequence set out in FIGS. 1A-B (SEQ ID NO:1).

The 3' primer has the following sequence:

5'CGC TCT AGA TCA AGC GTA GTC TGG GAC GTC GTA TGG GTA TCT ATC AAA GTT GCT TTC3'(SEQ ID NO:9), containing the underlined XbaI restriction site, a stop codon, an HA tag, and 18 nucleotides reverse and complementary to nucleotides 619–639 of the TR1-like ligand II coding sequence set out in FIGS. 1A-B (SEQ ID NO:1).

The PCR amplified DNA fragment and the vector, pcDNAI/Amp, are digested with BamHI and XbaI and then ligated. The ligation mixture is transformed into E. Coli strain SURE (available from Stratagene Cloning Systems, 11099 North Torrey Pines Road, La Jolla, Calif. 92037) and the transformed culture is plated on ampicillin media plates which then are incubated to allow growth of ampicillin resistant colonies. Plasmid DNA is isolated from resistant colonies and examined by restriction analysis and gel sizing for the presence of the T1R-like ligand II encoding fragment.

For expression of recombinant T1R-like ligand II, COS cells are transfected with an expression vector, as described above, using DEAE-DEXTRAN, as described, for instance, in Sambrook et al., Molecular Cloning: A Laboratory Manual, Cold Spring Laboratory Press, Cold Spring Harbor, New York (1989). Cells are incubated under conditions for expression of T1R-like ligand II by the vector.

Expression of the T1R-like ligand II HA fusion protein is detected by radiolabelling and immunoprecipitation, using methods described in, for example Harlow et al., Antibodies: A Laboratory Manual, 2and Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al., cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls Example 3

(b): Cloning and Expression in CHO Cells

The vector pC4 is used for the expression of T1R-like ligand protein. Plasmid pC4 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC4 contains for the expression of the gene of interest a strong promoter of the long terminal repeat (LTR) of the Rouse Sarcoma Virus (Cullen, et al., Molecular and Cellular biology, March 1985, 438–4470) plus a fragment isolated from the enhancer of the immediate early gene of human cytomegalovirus (CMV) (Boshart et al., Cell 41:521–530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3' intron and the polyadenylation site of the rat preproinsulin gene. Other highly efficient promoters can also be used for the expression, e.g., the human P-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g. G418 plus methotrexate.

The plasmid pC4 is digested with the restriction enzyme BamHI and then dephosphorylated using calf intestinal phosphates by procedures known in the art. The vector is then isolated from a 1% agarose gel.

The DNA sequence encoding T1R-like ligand II protein is amplified using PCR oligonucleotide primers specific to the amino terminal sequence of the T1R-like ligand II protein and to vector sequences 3' to the gene. Additional nucleotides containing restriction sites to facilitate cloning are added to the 5' and 3' sequences respectively.

The cDNA sequence encoding the full length T1R-like ligand II in the deposited clone is amplified using PCR oligonucleotide primers corresponding to the 5' and 3' sequences of the gene. The 5' primer has the sequence 5'CGC GGATCC GCC ATC ATG GGC GAC AAG ATC TGG 3'(SEQ ID NO:6), containing the underlined BamH I restriction enzyme site followed 18 nucleotides (nucleotides 55–72) of the sequence of T1R like ligand II in FIGS. 1A-B (SEQ ID NO:1). Inserted into an expression vector, as described below, the 5' end of the amplified fragment encoding T1R-like ligand II provides an efficient signal peptide. An efficient signal for initiation of translation in eukaryotic cells, as described by Kozak, M., J. Mol. Biol. 196: 947–950 (1987) is appropriately located in the vector portion of the construct.

The 3' primer has the sequence 5'GCG GGT ACC TCA CAA TGT TAC GTA CTC TAG 3'(SEQ ID NO:7), containing the underlined Asp 718 restriction site followed by a stop codon and 18 nucleotides reverse and complementary to nucleotides 754 to 771 of the T1R-like ligand II coding sequence in FIGS. 1A-B (SEQ ID NO:1). The restriction sites are convenient to restriction enzyme sites in the CHO expression vector PC-4.

The cDNA sequence encoding the extracellular domain of the full length T1R-like ligand II in the deposited clone is amplified using PCR oligonucleotide primers corresponding to the 5' and 3' sequences of the gene.

The 5' primer has the sequence 5'CGC GGA TCC GCC ATC ATG GGC GAC AAG ATC TGG 3'(SEQ ID NO:1) containing the underlined BamHI restriction enzyme site and 18 nucleotides (nucleotides 55 to 72) of the T1R-like ligand H coding sequence in FIGS. 1A-B (SEQ ID NO:1). Inserted into an expression vector, as described below, the 5' end of the amplified fragment encoding T1R-like ligand II provides an efficient signal peptide. An efficient signal for initiation of translation in eukaryotic cells, as described by Kozak, M., *J. Mol. Biol.* 196: 947–950 (1987) is appropriately located in the vector portion of the construct.

The 3' primer has the sequence 5'CGC GGA TCC TCA TCT ATC AAA GTT GCT TTC 3'(SEQ ID NO:8) containing the underlined Asp 718 restriction site followed by a stop codon and 18 nucleotides reverse and complementary to nucleotides 619–614 of the T1R-like ligand II coding sequence set out in FIGS. 1A-B (SEQ ID NO:1).

The amplified T1R-like ligand II protein DNA are digested with BamHI and Asp 718. The vector pC4 is digested with BamHI and the digested DNAs are then ligated together. The isolated fragment and the dephosphorylated vector are then ligated with T4 DNA ligase. Insertion of the T1R like ligand II protein DNA into the BamHI restricted vector places the T1R like ligand II protein coding region downstream of and operably linked to the vector's promoter. *E. coli* HB101 cells are then transformed and bacteria identified that contained the plasmid pC4 inserted in the correct orientation using the restriction enzyme BamHI. The ligation mixture is transformed into competent *E. coli* cells using standard procedures as described, for example, in Sambrook et al., MOLECULAR CLONING: A LABORATORY MANUAL, 2and Ed.; Cold Spring Harbor Laboratory *Press, Cold Spring Harbor, N.Y.* (1989). The transformed culture is plated on ampicillin media plates which then are incubated to allow growth of ampicillin resistant colonies. Plasmid DNA is isolated from resistant colonies and examined by restriction analysis and gel sizing for the presence of the T1R-like ligand II-encoding fragment. The sequence of the inserted gene is confirmed by DNA sequencing.

Transfection of CHO-DHFR-cells

Chinese hamster ovary cells lacking an active DHFR enzyme are used for transfection 5 µg of the expression plasmid C4 are cotransfected with 0.5 µg of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 µM, 2 µM, 5 µM). The same procedure is repeated until clones grow at a concentration of 100 µM.

The expression of the desired gene product is analyzed by Western blot analysis and SDS-PAGE. Expression of the T1R-like ligand II fusion protein is detected by radiolabelling and immunoprecipitation, using methods described in, for example Harlow et al., Antibodies: A Laboratory Manual, 2and Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al., cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 4

Tissue Distribution of T1R-like Ligand II Gene Expression

Northern blot analysis is carried out to examine expression levels of the 1R-like ligand II gene in human tissues, using methods described by, among others, Sambrook et al., cited above. A cDNA probe containing the entire T1R-like ligand II nucleotide sequence (SEQ ID NO:1) is labeled with $^{32}$P using the rediprime™ DNA labelling system (Amersham Life Science), according to manufacturer's instructions. After labelling, the probe is purified using a CHROMA SPIN-100™ column (Clontech Laboratories, Inc.), according to manufacturer's protocol number PT1200-1. The purified labelled probe is then used to examine various human tissues for expression of the T1R-like ligand II gene.

Multiple Tissue Northern (MTN) blots containing various human tissues (H) and human immune system tissues (IM) are obtained from Clontech and are examined with labelled probe using ExpressHyb™ Hybridization Solution (Clontech) according to manufacturer's protocol number PT 1190-1. Following hybridization and washing, the blots are mounted and exposed to film at −70° C. overnight, and films developed according to standard procedures.

It will be clear that the invention may be practiced otherwise than as particularly described in the foregoing description and examples.

Numerous modifications and variations of the present invention are possible in light of the above teachings and, therefore, are within the scope of the appended claims.

The disclosures of all patents, patent applications, and publications referred to herein are hereby entirely incorporated by reference.

What is claimed is:

1. An isolated polynucleotide comprising a nucleotide sequence selected from the group consisting of:
   (a) a nucleotide sequence encoding amino acids −26 to 203 of SEQ ID NO:2;
   (b) a nucleotide sequence encoding amino acids −25 to 203 of SEQ ID NO:2;
   (c) a nucleotide sequence encoding amino acids 1 to 203 of SEQ ID NO:2;
   (d) a nucleotide sequence encoding the complete polypeptide as encoded by the cDNA clone contained in ATCC Deposit No. 97655;
   (e) a nucleotide sequence encoding the mature polypeptide as encoded by the cDNA clone contained in ATCC Deposit No. 97655; and
   (f) the complement of (a), (b), (c), (d), or (e).

2. The isolated polynucleotide of claim 1, wherein said nucleotide sequence is (a).

3. The isolated polynucleotide of claim 2, which comprises nucleotides 55 to 741 of SEQ ID NO:1.

4. The isolated polynucleotide of claim 1, wherein said nucleotide sequence is (b).

5. The isolated polynucleotide of claim 4, which comprises nucleotides 58 to 741 of SEQ ID NO:1.

6. The isolated polynucleotide of claim 1, wherein said nucleotide sequence is (c).

7. The isolated polynucleotide of claim 6, which comprises nucleotides 133 to 741 of SEQ ID NO:1.

8. The isolated polynucleotide of claim 1, wherein said nucleotide sequence is (d).

9. The isolated polynucleotide of claim 1, wherein said nucleotide sequence is (e).

10. The isolated polynucleotide of claim 1, wherein said nucleotide sequence is (f).

11. The isolated polynucleotide of claim 1, which is DNA.

12. The isolated polynucleotide of claim 1, which is RNA.

13. The isolated polynucleotide of claim 1, further comprising a heterologous polynucleotide.

14. The isolated polynucleotide of claim 13, wherein said heterologous polynucleotide encodes a heterologous polypeptide.

15. A method for making a vector, comprising inserting the isolated polynucleotide of claim 1 into a vector.

16. The vector produced by the method of claim 15.

17. The vector of claim 16, which is a plasmid.

18. The vector of claim 16, which is a baculovirus.

19. The vector of claim 16, wherein said isolated polynucleotide is operatively associated with a heterologous regulatory sequence that controls gene expression.

20. A genetically engineered host cell comprising the isolated polynucleotide of claim 1.

21. The genetically engineered host cell of claim 20, wherein said isolated polynucleotide is operatively associated with a regulatory sequence that controls gene expression.

22. The genetically engineered host cell of claim 21, which is *E. coli*.

23. The genetically engineered host cell of claim 21, which is a COS cell.

24. The genetically engineered host cell of claim 21, which is a CHO cell.

25. A method of producing a T1 receptor-like ligand II olypeptide, comprising culturing the host cell of claim 21 under conditions such that said polypeptide is expressed, and recovering said polypeptide.

26. An isolated polynucleotide comprising 250 contiguous nucleotides of the coding region of SEQ ID NO:1, provided that said isolated polynucleotide does not have the nucleotide sequence of any one of SEQ ID NOs:12–25.

27. The isolated polynucleotide of claim 26, which comprises 350 contiguous nucleotides of the coding region of SEQ ID NO:1.

28. The isolated polynucleotide of claim 27, which comprises 500 contiguous nucleotides of the coding region of SEQ ID NO:1.

29. An isolated polynucleotide comprising a first polynucleotide which hybridizes at 42° C. in 50% formamide, 5×SSC, 50 mM sodium phosphate, 5×Denhardt's solution, 10% dextran sulfate, and 20 µg/ml denatured, sheared salmon sperm DNA, followed by washing in 0.1×SSC at 65° C., to a second polynucleotide having the nucleotide sequence of the coding region of SEQ ID NO:1, or the complement thereof, wherein said first polynucleotide is 250 or more nucleotides long; and wherein said first polynucleotide does not have the nucleotide sequence of any one of SEQ ID NOs:12–25.

30. The isolated polynucleotide of claim 29, wherein said first polynucleotide is 500 or more nucleotides long.

31. The isolated polynucleotide of claim 29, wherein said first polynucleotide hybridizes to a polynucleotide having nucleotides 133 to 636 of SEQ ID NO:1.

32. The isolated polynucleotide of claim 29, wherein said first polynucleotide hybridizes to a polynucleotide having nucleotides 637 to 705 of SEQ ID NO:1.

33. The isolated polynucleotide of claim 29, wherein said first polynucleotide hybridizes to a polynucleotide having nucleotides 706 to 741 of SEQ ID NO:1.

34. A method for making a vector, comprising inserting the isolated polynucleotide of claim 29 into a vector.

35. The vector produced by the method of claim 34.

36. A genetically engineered host cell comprising the isolated polynucleotide of claim 29.

37. An isolated polynucleotide comprising a nucleotide sequence selected from the group consisting of (a) a nucleotide sequence encoding amino acids 1 to 168 of SEQ ID NO:2;

(b) a nucleotide sequence encoding amino acids 192 to 203 of SEQ ID NO:2; and (c) a nucleotide sequence encoding the extracellular and intracellular domains of the T1 receptor-like ligand II with all or part of the transmembrane domain deleted.

38. The isolated polynucleotide of claim 37, wherein said nucleotide sequence is (a).

39. The isolated polynucleotide of claim 37, wherein said nucleotide sequence is (b).

40. The isolated polynucleotide of claim 37, wherein said nucleotide sequence is (c).

41. An isolated polynucleotide comprising a first nucleotide sequence 95% or more identical to a second nucleotide sequence selected from the group consisting of:

(a) a nucleotide sequence encoding amino acids −26 to 203 of SEQ ID NO:2;

(b) a nucleotide sequence encoding amino acids −25 to 203 of SEQ ID NO:2;

(c) a nucleotide sequence encoding amino acids 1 to 203 of SEQ ID NO:2;

(d) a nucleotide sequence encoding the complete polypeptide as encoded by the cDNA clone contained in ATCC Deposit No. 97655;

(e) a nucleotide sequence encoding the mature polypeptide as encoded by the cDNA clone contained in ATCC Deposit No. 97655; and (f) the complement of (a), (b), (c), (d), or (e);

wherein percent identity is calculated using BESTFIT with the parameters set such that percentage of identity is calculated over the full length of the reference nucleotide sequence and that gaps in homology of up to 5% of the total number of nucleotides in the reference sequence are allowed.

42. The isolated polynucleotide of claim 41, wherein said second nucleotide sequence is (a).

43. The isolated polynucleotide of claim 41, wherein said second nucleotide sequence is (b).

44. The isolated polynucleotide of claim 41, wherein said second nucleotide sequence is (c).

45. The isolated polynucleotide of claim 41, wherein said second nucleotide sequence is (d).

46. The isolated polynucleotide of claim 41, wherein said second nucleotide sequence is (e).

47. The isolated polynucleotide of claim 41, wherein said second nucleotide sequence is (f).

48. The isolated polynucleotide of claim 41, further comprising a heterologous polynucleotide.

49. The isolated polynucleotide of claim 48, wherein said heterologous polynucleotide encodes a heterologous polypeptide.

50. A method of making a vector, comprising inserting the isolated polynucleotide of claim 41 into a vector.

51. The vector produced by the method of claim 50.

52. The vector of claim 51, which is a plasmid.

53. The vector of claim 51, which is a baculovirus.

54. The vector of claim 51, wherein said isolated polynucleotide is operatively associated with a heterologous regulatory sequence that controls gene expression.

55. A genetically engineered host cell comprising the isolated polynucleotide of claim 41.

56. The genetically engineered host cell of claim 55, wherein said isolated polynucleotide is operatively associated with a regulatory sequence that controls gene expression.

57. The genetically engineered host cell of claim 56, which is *E. coli*.

58. The genetically engineered host cell of claim 56, which is a COS cell.

59. The genetically engineered host cell of claim 56, which is a CHO cell.

60. The isolated nucleic acid molecule of claim 42, wherein said second nucleotide sequence is nucleotides 55 to 741 of SEQ ID NO:1.

61. The isolated nucleic acid molecule of claim 43, wherein said second nucleotide sequence is nucleotides 58 to 741 of SEQ ID NO:1.

62. The isolated nucleic acid molecule of claim 44, wherein said second nucleotide sequence is nucleotides 133 to 741 of SEQ ID NO:1.

* * * * *

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
       (A) LENGTH: 1244 base pairs
       (B) TYPE: nucleic acid
       (C) STRANDEDNESS: both
       (D) TOPOLOGY: linear (ii) MOLECULE TYPE: cDNA (ix) FEATURE:
       (A) NAME/KEY: CDS
       (B) LOCATION: 55..741

(ix) FEATURE:
       (A) NAME/KEY: sig_peptide
       (B) LOCATION: 55..130

(ix) FEATURE:
       (A) NAME/KEY: mat_peptide
       (B) LOCATION: 133..741

(xi) SEQUENCE DESCRIPTION: SEQ ID NO:1:

```
CACGAGGACA ACAGTACCTG ACGCCTCTTT CAGCCCGGGA TCGCCCCAGC AGGG ATG                57
                                                              Met
                                                              -26

GGC GAC AAG ATC TGG CTG CCC TTC CCC GTG CTC CTT CTG GCC GCT CTG               105
Gly Asp Lys Ile Trp Leu Pro Phe Pro Val Leu Leu Leu Ala Ala Leu
-25                 -20                 -15                 -10

CCT CCG GTG CTG CTG CCT GGG GCG GCC GGC TTC ACA CCT TCC CTC GAT               153
Pro Pro Val Leu Leu Pro Gly Ala Ala Gly Phe Thr Pro Ser Leu Asp
                -5                   1               5

AGC GAC TTC ACC TTT ACC CTT CCC GCC GGC CAG AAG GAG TGC TTC TAC               201
Ser Asp Phe Thr Phe Thr Leu Pro Ala Gly Gln Lys Glu Cys Phe Tyr
            10                  15                  20

CAG CCC ATG CCC CTG AAG GCC TCG CTG GAG ATC GAG TAC CAA GTT TTA               249
Gln Pro Met Pro Leu Lys Ala Ser Leu Glu Ile Glu Tyr Gln Val Leu
        25                  30                  35

GAT GGA GCA GGA TTA GAT ATT GAT TTC CAT CTT GCC TCT CCA GAA GGC               297
Asp Gly Ala Gly Leu Asp Ile Asp Phe His Leu Ala Ser Pro Glu Gly
    40                  45                  50                  55

AAA ACC TTA GTT TTT GAA CAA AGA AAA TCA GAT GGA GTT CAC ACT GTA               345
Lys Thr Leu Val Phe Glu Gln Arg Lys Ser Asp Gly Val His Thr Val
                60                  65                  70

GAG ACT GAA GTT GGT GAT TAC ATG TTC TGC TTT GAC AAT ACA TTC AGC               393
Glu Thr Glu Val Gly Asp Tyr Met Phe Cys Phe Asp Asn Thr Phe Ser
            75                  80                  85

ACC ATT TCT GAG AAG GTG ATT TTC TTT GAA TTA ATC CTG GAT AAT ATG               441
Thr Ile Ser Glu Lys Val Ile Phe Phe Glu Leu Ile Leu Asp Asn Met
        90                  95                  100

GGA GAA CAG GCA CAA GAA CAA GAA GAT TGG AAG AAA TAT ATT ACT GGC               489
Gly Glu Gln Ala Gln Glu Gln Glu Asp Trp Lys Lys Tyr Ile Thr Gly
    105                 110                 115

ACA GAT ATA TTG GAT ATG AAA CTG GAA GAC ATC CTG GAA TCC ATC AAC               537
Thr Asp Ile Leu Asp Met Lys Leu Glu Asp Ile Leu Glu Ser Ile Asn
120                 125                 130                 135

AGC ATC AAG TCC AGA CTA AGC AAA AGT GGG CAC ATA CAA ACT CTG CTT               585
Ser Ile Lys Ser Arg Leu Ser Lys Ser Gly His Ile Gln Thr Leu Leu
                140                 145                 150
```

```
AGA GCA TTT GAA GCT CGT GAT CGA AAC ATA CAA GAA AGC AAC TTT GAT         633
Arg Ala Phe Glu Ala Arg Asp Arg Asn Ile Gln Glu Ser Asn Phe Asp
            155                 160                 165

AGA GTC AAT TTC TGG TCT ATG GTT AAT TTA GTG GTC ATG GTG GTG GTG         681
Arg Val Asn Phe Trp Ser Met Val Asn Leu Val Val Met Val Val Val
            170                 175                 180

TCA GCC ATT CAA GTT TAT ATG CTG AAG AGT CTG TTT GAA GAT AAG AGG         729
Ser Ala Ile Gln Val Tyr Met Leu Lys Ser Leu Phe Glu Asp Lys Arg
            185                 190                 195

AAA AGT AGA ACT TAAAACTCCA AACTAGAGTA CGTAACATTG AAAAATGAGG             781
Lys Ser Arg Thr
200

CATAAAAATG CCATAAACTG TTACAGTCCA GACCATTAAT GGTCTTCTCC AAAATATTTT       841

GAGATATAAA AGTAGGAAAC AGGTATAATT TTAATGTGAA AATTAAGTCT TCACTTTCTG       901

TGCAAGTAAT CCTGCTGATC CAGTTGTACT TAAGTGTGTA ACAGGAATAT TTTGCAGAAT       961

ATAGGTTTAA CTGAATGAAG CCATATTAAT AACTGCATTT TCCTAACTTT GAAAAATTTT     1021

GCAAATGTCT TAGGTGATTT AAATAAATGA GTATTGGGCC TAATTGCAAC ACCAGTCTGT     1081

TTTTAACAGG TTCTATTACC CAGAACTTTT TTGTAAATGC GGCAGTTACA AATTAACTGT     1141

GGAAGTTTTC AGTTTTAAGT TATAAATCAC CTGAGAATTA CCTAATGATG GATTGAATAA     1201

ATCTTTAGAC TACAAAAAAA AAAAAAAAAA AAAAAAAAA AAA                        1244

(2) INFORMATION FOR SEQ ID NO:2:

(i) SEQUENCE CHARACTERISTICS:
        (A) LENGTH: 229 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Asp Lys Ile Trp Leu Pro Phe Pro Val Leu Leu Ala Ala
-26 -25             -20             -15

Leu Pro Pro Val Leu Leu Pro Gly Ala Ala Gly Phe Thr Pro Ser Leu
-10              -5              1               5

Asp Ser Asp Phe Thr Phe Thr Leu Pro Ala Gly Gln Lys Glu Cys Phe
            10              15              20

Tyr Gln Pro Met Pro Leu Lys Ala Ser Leu Glu Ile Glu Tyr Gln Val
        25              30              35

Leu Asp Gly Ala Gly Leu Asp Ile Asp Phe His Leu Ala Ser Pro Glu
    40              45              50

Gly Lys Thr Leu Val Phe Glu Gln Arg Lys Ser Asp Gly Val His Thr
55              60              65              70

Val Glu Thr Glu Val Gly Asp Tyr Met Phe Cys Phe Asp Asn Thr Phe
            75              80              85

Ser Thr Ile Ser Glu Lys Val Ile Phe Phe Glu Leu Ile Leu Asp Asn
            90              95              100

Met Gly Glu Gln Ala Gln Glu Gln Glu Asp Trp Lys Lys Tyr Ile Thr
            105             110             115

Gly Thr Asp Ile Leu Asp Met Lys Leu Glu Asp Ile Leu Glu Ser Ile
        120             125             130

Asn Ser Ile Lys Ser Arg Leu Ser Lys Ser Gly His Ile Gln Thr Leu
135             140             145             150

Leu Arg Ala Phe Glu Ala Arg Asp Arg Asn Ile Gln Glu Ser Asn Phe
```

```
                155              160              165
Asp Arg Val Asn Phe Trp Ser Met Val Asn Leu Val Val Met Val Val
            170              175              180

Val Ser Ala Ile Gln Val Tyr Met Leu Lys Ser Leu Phe Glu Asp Lys
        185              190              195

Arg Lys Ser Arg Thr
    200
```

(2) INFORMATION FOR SEQ ID NO:3:

(i) SEQUENCE CHARACTERISTICS:
        (A) LENGTH: 227 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Met Ala Ala Gly Ala Ala Leu Ala Leu Ala Leu Trp Leu Leu Met
1               5                  10                  15

Pro Pro Val Glu Val Gly Gly Ala Gly Pro Pro Ile Gln Asp Gly
            20              25              30

Glu Phe Thr Phe Leu Leu Pro Ala Gly Arg Lys Gln Cys Phe Tyr Gln
        35              40              45

Ser Ala Pro Ala Asn Ala Ser Leu Glu Thr Glu Tyr Gln Val Ile Gly
    50              55              60

Gly Ala Gly Leu Asp Val Asp Phe Thr Leu Glu Ser Pro Gln Gly Val
65              70              75              80

Leu Leu Val Ser Glu Ser Arg Lys Ala Asp Gly Val His Thr Val Glu
            85              90              95

Pro Thr Glu Ala Gly Asp Tyr Lys Leu Cys Phe Asp Asn Ser Phe Ser
        100             105             110

Thr Ile Ser Glu Lys Leu Val Phe Phe Glu Leu Ile Phe Asp Ser Leu
    115             120             125

Gln Asp Asp Glu Glu Val Glu Gly Trp Ala Glu Ala Val Glu Pro Glu
130             135             140

Glu Met Leu Asp Val Lys Met Glu Asp Ile Lys Glu Ser Ile Glu Thr
145             150             155             160

Met Arg Thr Arg Leu Glu Arg Ser Ile Gln Met Leu Thr Leu Leu Arg
            165             170             175

Ala Phe Glu Ala Arg Asp Arg Asn Leu Gln Glu Gly Asn Leu Glu Arg
        180             185             190

Val Asn Phe Trp Ser Ala Val Asn Val Ala Val Leu Leu Leu Val Ala
    195             200             205

Val Leu Gln Val Cys Thr Leu Lys Arg Phe Phe Gln Asp Lys Arg Pro
    210             215             220

Val Pro Thr
225
```

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CGCCCATGGC CGGCTTCACA CCTTCC                                        26

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CGCAAGCTTT CATCTATCAA AGTTGCTTTC                                    30

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CGCGGATCCG CCATCATGGG CGACAAGATC TGG                                33

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CGCGGTACCT CACAATGTTA CGTACTCTAG                                    30

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CGCGGTACCT CATCTATCAA AGTTGCTTTC                                    30

(2) INFORMATION FOR SEQ ID NO:9:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CGCTCTAGAT CAAGCGTAGT CTGGGACGTC GTATGGGTAT CTATCAAAGT TGCTTTC      57

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

```
TGACAGAGGG ACTTTCCGAG AGGA                                       24
```

(2) INFORMATION FOR SEQ ID NO:11:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
AATTCGGCAC GAGCTTCTAC CAGCCCATGC CCCTNAAGGC CTCGCTGGAG ATCGAGTACC   60
AAGTTTTAGA TGGAGCAGGA TTAGATATTG ATTTCCCATC TTGCCTCTCC AGAAGGCAAA  120
ACCTTAGTTT TTGAACAAAG AAAATCAGAT GGAGTTCACA CGTGTATAAG AAGTAAAAAT  180
GGGCCAGGCA CTGCGGTTCA CGCCTATAAT CCCAGCACTT TCCGAGGCCG AGTGTAGAGA  240
CTGAAGTTGG TGATTACATG TTCTGCTTTG ACAATACATT CAGCACCATT TCTGAGAAGG  300
TGATTTTCTT TGAATTAATC CTGGATAATA TGGGAGGACA GGCACAAGAC AAGAGGTTTG  360
GAGNATATTT ACTGGCCNAT TTATGGTATG                                  390
```

(2) INFORMATION FOR SEQ ID NO:12:

(i) SEQUENCE CHARACTERISTICS:
        (A) LENGTH: 530 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
AGACTCCAGA TTTCCCTGTC AACCACGAGG AGTCCAGAGA GGAAACGCGG AGANGAACAA   60
CAGTACCTGA CGCCTCTTTC AGCCCGGGAT CGCCCCAGCA GGGATGGGCG ACAAGATCTG  120
GCTGCCCTTC CCCGTGCTCC TTCTGGCCGC TCTGCCTCCG GTGCTGCTGC CTNGGGNCGG  180
CCGGCTTCAC ACCTTCCCTC GATAGCGACT TCACCTTTAC CCTTCCCGCC GGCCAGAAGG  240
AGTGCTTCTA CCAGCCCATG CCCCTGAAGG CCTCGCTGGA GATCGAGTAC CAAGTTTTAG  300
ATGGAGCAGG ATTAGATATT GATTTCCATC TTGCCTCTCC AGAAGGCAAA ACCTTAGTTT  360
TTGAACAAAG AAAATCAGAT GGAGTTCACA CTGTAGAGAC TGAAGTTGGT GATTACATGT  420
TCTGCTTTGA CAATACATTC AGCACCATTT CTGAGAAGGT GATTTTCTTT GAATTAATCC  480
TGGATAATAT GGGAGAACAG GCACAAGAAC AAGAAGATTG GAAGAAATAT             530
```

(2) INFORMATION FOR SEQ ID NO:13:

(i) SEQUENCE CHARACTERISTICS:
        (A) LENGTH: 463 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
AGACTCCAGA TTTCCCTGTC AACCACGAGG AGTCCAGAGA GGAAACGCGG AGCGCACAAC        60

AGTACCTGAC GCCTCTTTCA GCCCGGGATC GCCCCAGCAG GGATGGGCGA CAAGATCTGG       120

CTGCCCTTCC CCGTGCTCCT TCTGGCCGCT CTGCCTCCGG TGCTGCTGCC TGGGGCGGCC       180

GGCTTCACAC CTTCCCTCGA TAGCGACTTC ACCTTTACCC TTCCCGCCGG CCAGAAGGAG       240

TGCTTCTACC AGCCCATGCC CCTGAAGGCC TCGCTGGAGA TCGAGTACCA AGTTTTAGAT       300

GGAGCAGGAT TAGATATTGA TTTCCATCTT GCCTCTCCAG AAGGCAAAAC CTTAGTTTTT       360

GAACAAAGAA AATCAGATGG AGTTCACACT GTAGAGACTG AAGTTGGTGA TTACATGTTC       420

TGCTTTGACA ATACATTCAG CACCATTTCT GAGAAGGTGA TTT                         463
```

(2) INFORMATION FOR SEQ ID NO:14:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
GCAGAATATA GGTTTAACTG AATGAAGCCA TATTAATAAC TGCATTTGCC TAACTTGGAA        60

AAGTTTGGCA AATGTCTTAG GTGATTTAAA TAAATGAGTA TTGGGCCTAA TTGCCACACC       120

AGTCTGTTTT GAACAGGTTC TATTACCCAG AACTTTTTTG TAAATGCGGC AGTTACAAAT       180

TAACTGTTGG AGGTTT                                                      196
```

(2) INFORMATION FOR SEQ ID NO:15:

(i) SEQUENCE CHARACTERISTICS:
        (A) LENGTH: 520 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
GCAAAACCTT AGTTTTTGAA CAAAGAAAAT CAGATGGAGT TCACACTGTA GAGACTGAAG        60

TTGGTGATTA CATGTTCTGC TTTGACAATA CATTCAGCAC CATTTCTGAG AAGGTGATTT       120

TCTTTGAATT AATCCTGGAT AATATGGGAG AACAGGCACA AGAACAAGAA GATTGGAAGA       180

AATATATTAC TGGCACAGAT ATATTGGATA TGAAACTGGA AGACATCCTG GAATCCATCA       240

ACAGCATCAA GTCCAGACTA AGCAAAAGTG GGCACATACA AACTCTGCTT AGAGCATTTG       300

AAGCTCGTGA TCGAAACATA CAAGAAAGCA ACTTTGATAG AGTCAATTTC TGGTCTATGG       360

TTAATTTAGT GGTCATGGTG GTGGTGTCAG CCATTCAAGT TTATATGCTG AAGAGTCTGG       420

TTTGAAGATN AGGAGGGAAA GTTGGAACTT AAAACTCCCA AACTTGGGTA CGGNACCTTG       480

NAAAATGGGG CCATTAAAAA TGCCATTAAC NGGTTCCAGC                             520
```

(2) INFORMATION FOR SEQ ID NO:16:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
AGACTCCAGA TTTCCCTGTC AACCACGAGG AGTCCAGAGA GGAAACGCGG AGATGAACAA      60

CAGTACCTGA CGCCTCTTTC AGCCCGGGAT CGCCCCAGCA GGGATGGGCG ACAAGATCTG     120

GCTGCCCTTC CCCGTGCTCC TTCTGGCCGC TCTGCCTCCG GTGCTGCTGC CTGGGNGGCC     180

GGCTTCACAC CTTCCCTCGA TAGCGACTTC ACCTTTACCC TTCCCGCCGG CCAGAAGGAG     240

TGCTTCTACC AGCCCATGCC CCTGAAGGCC TCGCTGGAGA TCGAGTACCA AGTTTTAGAT     300

GGAGCAGGAT TAGATATTGA TTTCCATCTT GCCTCTCCAG AAGGCAAAAC CTTAGTTTTT     360

GAACAAAGAA AATCAGATGG GAGTTCACAC TGTAAGAGAC TGAAGTTGGG TGATTACATG     420

TTCTGCTTTG ACAATACATT CAGCACCATT TCTGAGAAGG TGATTTCTTT GGAATTA       477
```

(2) INFORMATION FOR SEQ ID NO:17:

(i) SEQUENCE CHARACTERISTICS:
        (A) LENGTH: 403 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
GTAGTCTAAA GATTTATTCA ATCCATCATT AGGTAATTCT CAGGTGATTT ATAACTTAAA      60

ACTGAAAACT TCCACAGTTA ATTTGTAACT GCCGCATTTA CAAAAAAGTT CTGGGTAATA     120

GAACCTGTTA AAAACAGACT GGTGTTGCAA TTAGGCCCAA TACTCATTTA TTTAAATCAC     180

CTAAGACATT TGCAAAATTT TTCAAAGTTA GGAAAATGCA GTTATTAATA TGGCTTCATT     240

CAGTTAAACC TATATTCTGC AAAATATTCC TGTTACACAC TTAAGGTACA ACTGGATCAG     300

CAGGATTACT TGCACAGAAA GNTGAAGACT TAATTTTCAC ATTAAAATTA TACCTGGTTT     360

CCTACTTTTA TATCNCAAAA TATTTTGGGA GAAGACCATT AAT                       403
```

(2) INFORMATION FOR SEQ ID NO:18:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
TACCTGACGC CTCTTTCAGC CCGGGATCGC CCCAGCAGGA ATGGGCGACA AGATCTGGCT      60

GCCCTTCCCG TGCTCCTTCT GGCCGCTCTG CTCCGGTGCT GCTGCCTGGG NGGCCGGCTT     120

CACACCTTCC CTCGATAGCG ACTTCACCTT TACCTTCCGC CGGCAGAAGG AGTGCTNCTA     180

CCAGCCATGC NCCTGAAGGC CTCNCTGGAG ATCGAGTACC AAGTTTTAGA TGGAGCAGGA     240

TTAGATATTG ATTTCCATCT TGCCTCTCCA GAAAAGGCAA AACCTTAAGT TTTTGAACAA     300

AGAAATCAGA TGGAGTTCAC ACTGTAGAGA CTGAAAGTTG GTGATTACAT GTTCTGCTTT     360

GACAATACAT TCAAGAACCA TTTCTGAGAA GGTGAT                                396
```

(2) INFORMATION FOR SEQ ID NO:19:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
CCAGAAGGAG TGCTTCTACC AGCCCATGCC CCGTGAAGGC CTCGCTGGAG ATCGAGTACC      60

AAGTTTTAGA TGGAGCAGGA TTAGATATTG ATTTCCATCT TGCCTCTCCA GAAGGCAAAA     120

CCTTAGTTTT TGAACAAAGA AAATCAGATG GAGTTCACAC TGTAGAGACT GAAGTTGGTG     180

ATTACATGTT CTGCTTTGAC AATACATTCA GCACCATTTC TGAGAAGGTG ATTTTCTTTG     240

AATTAATCCT GGATAATATG GGAGAACAAG GCACAAGAAC AAGAAGATTG GAAGAAATAT     300

ATTACTGGC                                                             309
```

(2) INFORMATION FOR SEQ ID NO:20:

(i) SEQUENCE CHARACTERISTICS:
        (A) LENGTH: 462 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

```
ATTGATTTCC ATCTTGCCTC TCCAGAAGGC AAAACCTTAG TTTTTGAACA AGAAAATCA       60

GATGGAGTTC ACACTGTAGA GACTGAAGTT GGTGATTACA TGTTCTGCTT TGACAATACA     120

TTCAGCACCA TTTCTGAGAA GGTGATTTTC TTTGAATTAA TCCTGGATAA TATGGGAGAA     180

CAGGCACAAG AACAAGAAGA TTGGAAGAAA TATATTACTG GCACAGATAT ATTGGATATG     240

AAACTGGAAG ACATCCTGGG AATCCATCAA CAGCATCAAG TCCAGACTAA GGCAAAGTG      300

GGGCACATAC AAACTCTGCT TAGGAGCATT TGGAAGGCTC GTGGATCCGA ACATTACAA      360

GGAAAGGCAA CTTTGGATTA GGAGTCCAAT TTCTGGGTCT ATGGGTTAAT TTAGTGGGTC     420

ATGGTGGTGG TGTTCAGCCT TCAGTTTATA TGGCTGGAGG NT                        462
```

(2) INFORMATION FOR SEQ ID NO:21:

(i) SEQUENCE CHARACTERISTICS:
        (A) LENGTH: 423 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
GCGCGGAGAN GGACAACAGT ACCTGACGCC TCTTTCAGCC CGGGATCGCC CCACCAGGGA      60

ATGGGCGACA AGATCTGGCT GCCCTTCCCC GTGCTCCTTC TGGCCGCTCT GCCTCCGGTG     120

CTGCTGCCTG GGGGCCGGC TTCACACCTT CCCTCGATAG CGACTTCACC TTTACCCTTC      180

CCGCCGGCCA GAAGGAGTGC TTCTACCAGC CCATGCCCCT GAAGGCCTCG CTGGGAGATC     240

GAGTACCAAG TTTTAGATGG AGCAGGATTA GATATTGATT CCATCTTGC CTCTCCAGAA      300

GGGCAAAACC TTAGTTTTTG AACAAAGGA AAATCAGGTG GAGTTTCAC ANTGTAGGAG       360
```

```
GATTGAAGTT GGGTGGATTT ACATGTTTCT GGTTTTTGAC AATTACATTT CAGGCACCNT      420

TTT                                                                    423

(2) INFORMATION FOR SEQ ID NO:22:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

CGCGGAGACG NATCAACAGT ACCTGACGCC TCTTTCAGCC CCGGATCGCC CCAGCAGGAT       60

TGGGCGACAA GATCTGGCTG CCCTTCCCCG TGCTCCTTCT GGCCGCTCTG CCTCCGGTGC      120

TGCTGCCTGG GGGGCCGGCT TCACACCTTC CCTCGATAGC GACTTCACCT TTACCCTTCC      180

CGCCGGCCAG AAGGAGTGCT TCTACCAGCC CATGCCCCTG AAGGCCTCGC TGGGAGATCG      240

AGTACCAAGT TTTAGATGGG AGCAGGATTA GATATTGATT TTCCATCTTG CCTCTCCAGA      300

AGGGCAAAAC CTTAGTTTTT TGAACAAAGG AAAATCAGGT GGGGAGTTTC ACAATGTAGG      360

AGGATTGAAG TTTGGGTGAT TTACATGTTT TTGCTTTTGA ACAATTACAT TTCAGGCANC      420

ATTTTTGAGG NAGGGTGAAT TTTCTTTGGA                                       450

(2) INFORMATION FOR SEQ ID NO:23:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

TAATAACTGC ATTTTCCTAA CTTTGAAAAA TTTTGCAAAT GTCTTAGGTG ATTTAAATAA       60

ATGAGTATTG GGCCTAATTG CAACACCAGT CTGTTTTTAA CAGGTTCTAT TACCCAGAAC      120

TTTTTTGTAA ATGCGGCAGT TACAAATTAA CTGTGGAAGT TTTCAGTTTT AAGTTATAAA      180

TCACCTGAGA ATTACCTAAT GATGGATTGA ATAAATCTTT AGACTACAAA AGCCCAACTT      240

TTCTCTATTT ACATATGCAT CTCTCCTATA ATGTAAATAG AATAATAGCT TTGAAATACA      300

ATTAGGTTTT TGAGATTTTT ATAACCAAAT ACATTTCAGT GTAACATATT AGCAGAAAGC      360

ATTAGTCCTT GGACTTTGCT TACATTCCCA AAAGCTGACA TT                         402

(2) INFORMATION FOR SEQ ID NO:24:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

TTCCATCTTG CCTCTCCAGA AGGCAAAACC TTAGTTTTTG AACAAAGAAA ATCAGATGGA       60

GTTCACACTG TAGAGACTGA AGTTGGTGAT TACATGTTCT GCTTTGACAA TACATTCAGC      120

ACCATTTCTG AGAAGGTGAT TTTCTTTGAA TTAATCCTGG ATAATATGGG AGAACAGGCA      180
```

```
                                                     -continued

CAGGAACAAG AGGATTGGGA GGAATATATT ACTGGCACAG ATATATTGGA TATGAACTGG      240

AGACATCTGG ATCATCACAG CATCAGTCCA GACTAGCAAA GTGGGCACAT CAACTCTCTT      300

AGGCATTTG                                                              309

(2) INFORMATION FOR SEQ ID NO:25:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

AGACTCCAGA TTTCCCTGTC AACCACGAGG AGTCCAGAGA GAAAACGCGG AGATGAGCAA        60

GCAGTACCTG ACGCCTCTTT CAGCCCGGGA TCGCCCCAGC AGGGATGGGC GACAAGATCT       120

GGCTGCCCTT CCCCGTGCTC CTTCTGGCCG CTCTGCCTCC GGTGCTGCTG CCTGGGCGGC       180

CGGCTTCACA CCTTCCCTCG ATAGCGACTT CACCTTTACC CTTCCCGCCG GCCAGAAGGA       240

GTGCTTCTAC CAGCCCATGC GCCTGAAAGC CTCTCTTGAG ATCGAG                      286
```